United States Patent [19]
Haase et al.

[11] Patent Number: 6,072,039
[45] Date of Patent: Jun. 6, 2000

[54] HYBRID POLYPEPTIDE COMPARING A BIOTINYLATED AVIDIN BINDING POLYPEPTIDE FUSED TO A POLYPEPTIDE OF INTEREST

[75] Inventors: Ferdinand Carl Haase, Chalfont; Dean Ervin Cress, Souderton, both of Pa.

[73] Assignee: Rohm and Haas Company, Philadelphia, Pa.

[21] Appl. No.: 07/687,819

[22] Filed: Apr. 19, 1991

[51] Int. Cl.$^7$ ............................. C07K 14/00; C12N 15/00
[52] U.S. Cl. ......................... 530/409; 530/402; 435/69.7
[58] Field of Search .................................. 530/402, 409; 435/69.1

[56] References Cited

U.S. PATENT DOCUMENTS

| | | | |
|---|---|---|---|
| 4,839,293 | 6/1989 | Cantor et al. ......................... | 435/320.1 |
| 5,874,239 | 2/1999 | Schatz .................................... | 435/69.1 |

OTHER PUBLICATIONS

Cronan, J.E. Jr., The Journal of Biological Chemistry (Jun. 25, 1990) "Biotination of Protein in vivo" vol. 265(18) pp. 10327–10333.

Berger, M. (1979) Methods in Enzymology "Antibodies that bind Biotin and Inhibit Biotin–Containing Enzymes" vol. 62, pp. 319–326.

Kohanski, R.A et al. (1985) Annals of the New York Academy of Sciences, "Receptor Affinity Chromatography", vol. 447, pp. 373–385.

Sambrook et al. Molecular Cloning. A Laboratory Manual. Cold Spring Harbor NY 1986.

Murtif et al. (1987) The Journal of Biological Chemistry "Mutagenesis Affecting the Carboxyl Terminus of the Biotinyl Subunit of Transcarboxylase" vol. 262 (24) pp. 11813–11816.

Maina, C.V. et al. (1988) Gene "An *Escherichia coli* vector to express and purify foreign proteins by fusion to and separation from maltose–binding protein" vol. 74, pp. 365–373.

Lowenadler, B et al. The EMBO Journal "Production of specific antibodies against protein A fusion protein" (1986) vol. 5(9), pp. 2393–2398.

Nagai, K. et al. (1984) Nature "Generation of β–globulin by sequence specific proteolysis of a hybrid protein produced in *Escherichia coli*" vol. 309, pp. 810–812.

*Primary Examiner*—Lisa B. Arthur
*Attorney, Agent, or Firm*—James G. Vouros

[57] ABSTRACT

A hybrid polypeptide is disclosed, comprising a polypeptide for attachment of a prosthetic group to avidin fused to at least one polypeptide of interest, and a method of making the same. The hybrid polypeptide is produced by recombinant DNA techniques, using a DNA expression vector composed of a DNA fragment coding for the polypeptide for attachment to avidin fused to DNA coding for one or more polypeptides of interest. The hybrid polypeptide may also contain linking amino acid sequences for cleavage of the polypeptide of interest from the polypeptide for attachment using an appropriate proteolytic or chemical reagent. The hybrid polypeptide is expressed in appropriate host cells transformed with the DNA expression vector encoding the hybrid polypeptide, and may be recovered from crude cell extracts in high yield and high purity using avidin affinity chromatography. Following avidin affinity purification, the polypeptide for attachment and polypeptide of interest may be cleaved to yield polypeptide of interest in a highly pure and highly active state.

22 Claims, 5 Drawing Sheets

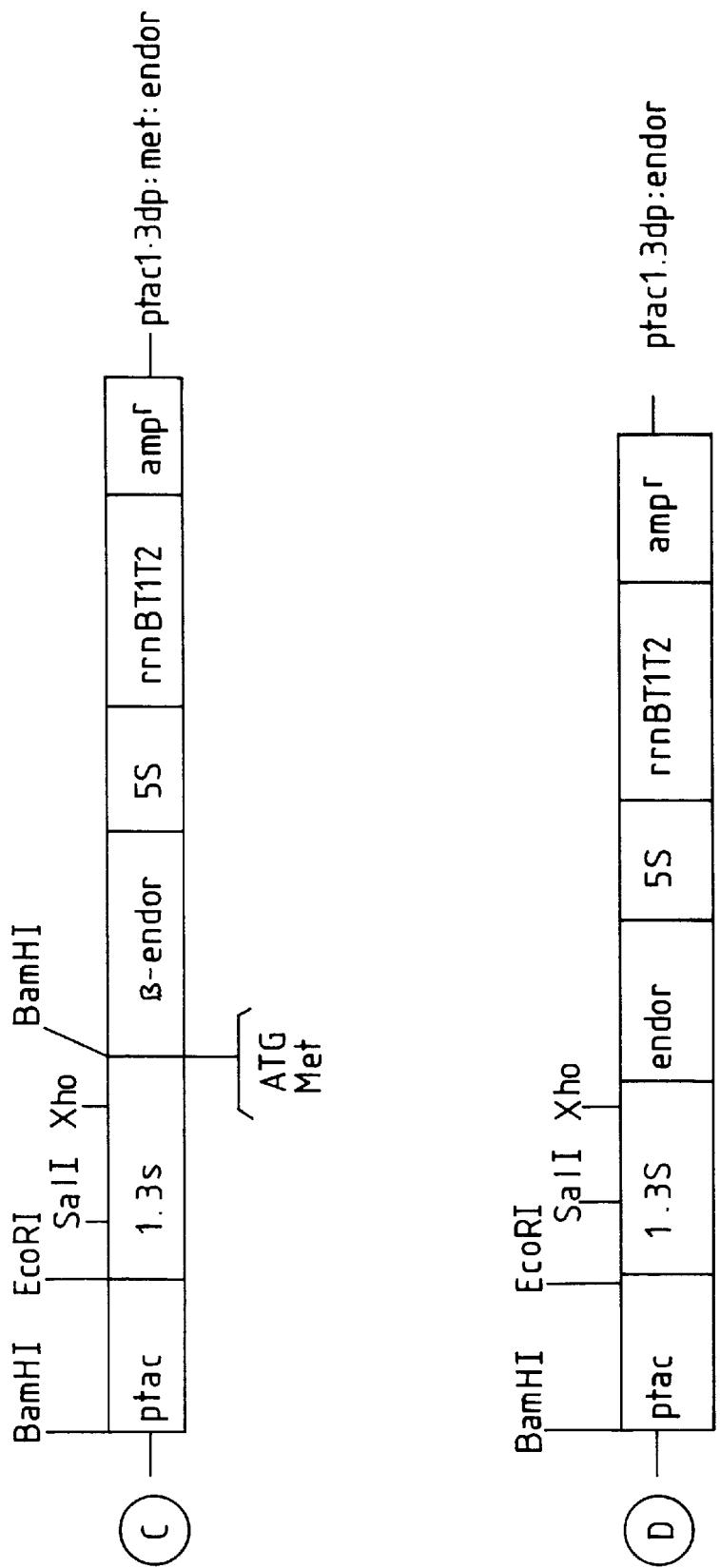

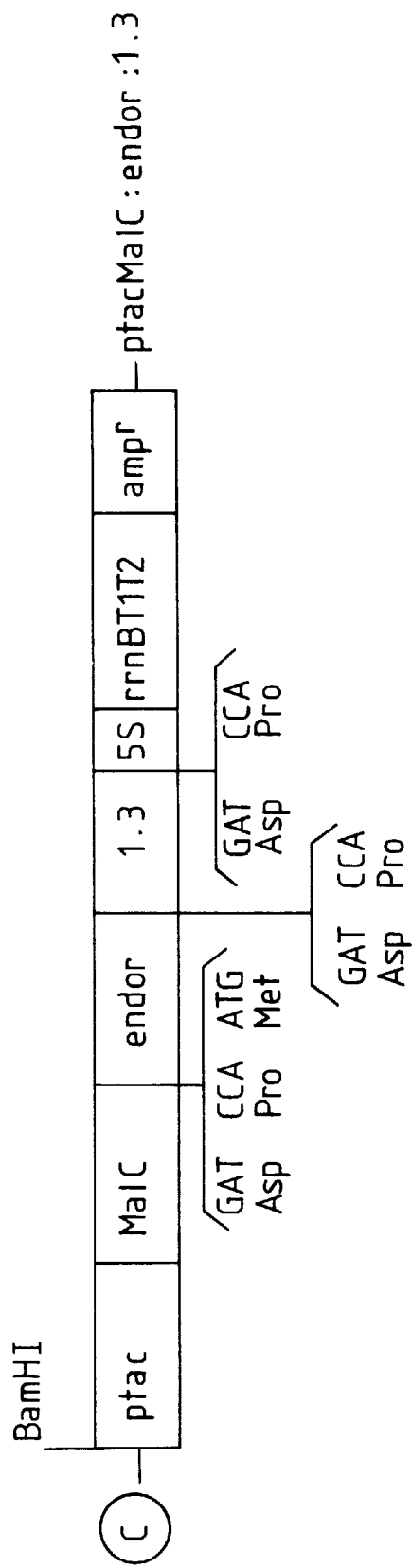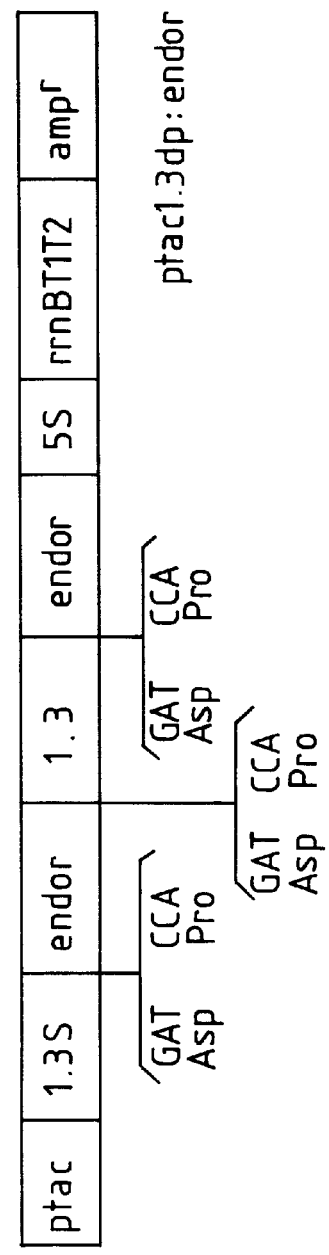

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
       (A) LENGTH: 123 amino acids
       (B) TYPE: amino acid
       (D) TOPOLOGY: linear (ii) MOLECULE TYPE: protein (vi) ORIGINAL SOURCE:
      (A) ORGANISM: Propionibacterium shermanii (x) PUBLICATION INFORMATION:
       (A) AUTHORS: Maloy, W L
          Bowien, B U
          Zwolinski, G K
          Kumar, K G
          Wood, H G
       (B) TITLE: Amino Acid Sequence of the Biotinyl Subunit
          from Transcarboxylase
       (C) JOURNAL: Journal of Biological Chemistry
       (D) VOLUME: 254
       (E) ISSUE: 22
       (F) PAGES: 11615-11622
       (G) DATE: Nov 26-1979
       (K) RELEVANT RESIDUES IN SEQ ID NO:1: FROM 1 TO 123

(xi) SEQUENCE DESCRIPTION: SEQ ID NO:1:

```
Met Lys Leu Lys Val Thr Val Asn Gly Thr Ala Tyr Asp Val Asp Val
1               5                   10                  15

Asp Val Asp Lys Ser His Glu Asn Pro Met Gly Thr Ile Leu Phe Gly
                20                  25                  30

Gly Gly Thr Gly Gly Ala Pro Ala Pro Arg Ala Ala Gly Gly Ala Gly
            35                  40                  45

Ala Gly Lys Ala Gly Glu Gly Glu Ile Pro Ala Pro Leu Ala Gly Thr
        50                  55                  60

Val Ser Lys Ile Leu Val Lys Glu Gly Asp Thr Val Lys Ala Gly Gln
65                  70                  75                  80

Thr Val Leu Val Leu Glu Ala Met Lys Met Glu Thr Glu Ile Asn Ala
                85                  90                  95

Pro Thr Asp Gly Lys Val Glu Lys Val Leu Val Lys Glu Arg Asp Ala
            100                 105                 110

Val Gln Gly Gly Gln Gly Leu Ile Lys Ile Gly
        115                 120
```

(2) INFORMATION FOR SEQ ID NO:2:

(i) SEQUENCE CHARACTERISTICS:
       (A) LENGTH: 43 amino acids
       (B) TYPE: amino acid
       (D) TOPOLOGY: linear (ii) MOLECULE TYPE: protein (v) FRAGMENT TYPE: internal (xi) SEQUENCE DESCRIPTION: SEQ ID NO:2:

```
Pro Ala Pro Leu Ala Gly Thr Val Ser Lys Ile Leu Val Lys Glu Gly
1               5                   10                  15

Asp Thr Val Lys Ala Gly Gln Thr Val Leu Val Leu Glu Ala Met Lys
                20                  25                  30
```

```
Met Glu Thr Glu Ile Asn Ala Pro Thr Asp Gly
         35                  40
```

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

```
GATCCATAAC GCCTAAGCTT                                              20
```

(2) INFORMATION FOR SEQ ID NO:4:

(i) SEQUENCE CHARACTERISTICS:
        (A) LENGTH: 372 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Propionibacterium shermanii
        (B) STRAIN: w52

(x) PUBLICATION INFORMATION:
        (A) AUTHORS: Murtif, V L
            Bahler, C R
            Samols, D
        (B) TITLE: Cloning and Expression of the 1.3S
            biotin-containing subunit of transcarboxylase
        (C) JOURNAL: Proc. Natl. Acad. Sci. U.S.A.
        (D) VOLUME: 82
        (E) ISSUE: Sept
        (F) PAGES: 5617-5621
        (G) DATE: 1985
        (K) RELEVANT RESIDUES IN SEQ ID NO:4: FROM 1 TO 372

(xi) SEQUENCE DESCRIPTION: SEQ ID NO:4:

```
ATGAAACTGA AGGTAACAGT CAACGGCACT GCGTATGACG TTGACGTTGA CGTCGACAAG      60

TCACACGAAA ACCCGATGGG CACCATCCTG TTCGGCGGCG GCACCGGCGG CGCGCCGGCA     120

CCGCGCGCAG CAGGTGGCGC AGGCGCCGGT AAGGCCGGAG AGGGCGAGAT TCCCGCTCCG     180

CTGGCCGGCA CCGTCTCCAA GATCCTCGTG AAGGAGGGTG ACACGGTCAA GGCTGGTCAG     240

ACCGTGCTCG TTCTCGAGGC CATGAAGATG GAGACCGAGA TCAACGCTCC CACCGACGGC     300

AAGGTCGAGA AGGTCCTTGT CAAGGAGCGT GACGCCGTGC AGGGCGGTCA GGGTCTCATC     360

AAGATCGGCT GA                                                        372
```

(2) INFORMATION FOR SEQ ID NO:5:

(i) SEQUENCE CHARACTERISTICS:
        (A) LENGTH: 390 base pairs
        (B) TYPE: nucleic acid
        (C) STRANDEDNESS: single
        (D) TOPOLOGY: linear (ii) MOLECULE TYPE: DNA (genomic)

(x) PUBLICATION INFORMATION:

(A) AUTHORS: Murtif, V L
                Samols, D
            (B) TITLE: Mutagenesis Affecting the Carboxyl Terminus
                of the Biotinyl Subunit of Transcarboxylase
            (C) JOURNAL: Journal of Biological Chemistry
            (D) VOLUME: 262
            (E) ISSUE: 24
            (F) PAGES: 11813-11816
            (G) DATE: Aug 25-1987
            (K) RELEVANT RESIDUES IN SEQ ID NO:5: FROM 1 TO 390

(xi) SEQUENCE DESCRIPTION: SEQ ID NO:5:

ATGAAACTGA AGGTAACAGT CAACGGCACT GCGTATGACG TTGACGTTGA CGTCGACAAG     60

TCACACGAAA ACCCGATGGG CACCATCCTG TTCGGCGGCG GCACCGGCGG CGCGCCGGCA    120

CCGCGCGCAG CAGGTGGCGC AGGCGCCGGT AAGGCCGGAG AGGGCGAGAT TCCCGCTCCG    180

CTGGCCGGCA CCGTCTCCAA GATCCTCGTG AAGGAGGGTG ACACGGTCAA GGCTGGTCAG    240

ACCGTGCTCG TTCTCGAGGC CATGAAGATG GAGACCGAGA TCAACGCTCC CACCGACGGC    300

AAGGTCGAGA AGGTCCTTGT CAAGGAGCGT GACGCCGTGC AGGGCGGTCA GGGTCTCATC    360

AAGATCGGCT GATCCATAAC GCCTAAGCTT                                    390

(2) INFORMATION FOR SEQ ID NO:6:

(i) SEQUENCE CHARACTERISTICS:
        (A) LENGTH: 31 amino acids
        (B) TYPE: amino acid
        (D) TOPOLOGY: linear (ii) MOLECULE TYPE: protein (xi) SEQUENCE DESCRIPTION: SEQ ID NO:6:

Tyr Gly Gly Phe Leu Thr Ser Glu Lys Ser Gln Thr Pro Leu Val Thr
1               5                   10                  15

Leu Phe Lys Asn Ala Ile Ile Lys Asn Ala Tyr Lys Lys Gly Glu
            20                  25                  30

(2) INFORMATION FOR SEQ ID NO:7:

(i) SEQUENCE CHARACTERISTICS:
        (A) LENGTH: 135 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

AAGCTTCTAG AGGATCCTAT GTACGGTGGT TTCCTGACCT CCGAAAAATC TCAGACCCCG     60

CTGGTTACTC TGTTCAAAAA CGCTATCATC AAAAACGCAT ACAAAAAAGG CGAATAAGGA    120

TCCGAATTCG AGCTC                                                    135

(2) INFORMATION FOR SEQ ID NO:8:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

AAGCTTCTAG AGGATCCTAT GTACGGTGGT TTCCTGACCT CCGAAAAATC TCAGACCCCG     60

```
CTGGTTACTC TGTTC                                                      75

(2) INFORMATION FOR SEQ ID NO:9:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: DNA (genomic), LOWER STRAND (xi) SEQUENCE DESCRIPTION: SEQ ID NO:9:

GAGCTCGAAT TCGGATCCTT ATTCGCCTTT TTTGTATGCG TTTTTGATGA TAGCGTTTTT     60

GAACAGAGTA ACCAG                                                      75

(2) INFORMATION FOR SEQ ID NO:10:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

AAGCTTCTAG AGATCGGCAT GTACGGTGGT TTCCTGACCT CCGAAAAATC TCAGACCCCG     60

CTGGTTACTC TGTTC                                                      75

(2) INFORMATION FOR SEQ ID NO:11:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: DNA (genomic), LOWER STRAND (xi) SEQUENCE DESCRIPTION: SEQ ID NO:11:

GAGCTCGAAT TCGGATCCTT ATTCGCCTTT TTTGTATGCG TTTTTGATGA TAGCGTTTTT     60

GAACAGAGTA ACCAG                                                      75

(2) INFORMATION FOR SEQ ID NO:12:

(i) SEQUENCE CHARACTERISTICS:
        (A) LENGTH: 135 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (iv) ANTI-SENSE: NO (xi) SEQUENCE DESCRIPTION: SEQ ID NO:12:

AAGCTTCTAG AGATCGGCAT GTACGGTGGT TTCCTGACCT CCGAAAAATC TCAGACCCCG     60

CTGGTTACTC TGTTCAAAAA CGCTATCATC AAAAACGCAT ACAAAAAAGG CGAATAAGGA    120

TCCGAATTCG AGCTC                                                     135

(2) INFORMATION FOR SEQ ID NO:13:
```

(i) SEQUENCE CHARACTERISTICS:
            (A) LENGTH: 75 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:13:

AAGCTTCTAG AGATCGGCTA CGGTGGTTTC CTGACCTCCG AAAAATCTCA GACCCCGCTG      60

GTTACTCTGT TCAAA                                                      75

(2) INFORMATION FOR SEQ ID NO:14:

(i) SEQUENCE CHARACTERISTICS:
            (A) LENGTH: 72 base pairs
            (B) TYPE: nucleic acid
            (C) STRANDEDNESS: single
            (D) TOPOLOGY: linear (ii) MOLECULE TYPE: DNA (genomic), LOWER STRAND (xi) SEQUENCE DESCRIPTION: SEQ ID NO:14:

GAGCTCGAAT TCGGATCCTT ATTCGCCTTT TTTGTATGCG TTTTTGATGA TAGCGTTTTT      60

GAACAGAGTA AC                                                         72

(2) INFORMATION FOR SEQ ID NO:15:

(i) SEQUENCE CHARACTERISTICS:
            (A) LENGTH: 132 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:15:

AAGCTTCTAG AGATCGGCTA CGGTGGTTTC CTGACCTCCG AAAAATCTCA GACCCCGCTG      60

GTTACTCTGT TCAAAAACGC TATCATCAAA AACGCATACA AAAAAGGCGA ATAAGGATCC     120

GAATTCGAGC TC                                                        132

(2) INFORMATION FOR SEQ ID NO:16:

(i) SEQUENCE CHARACTERISTICS:
            (A) LENGTH: 75 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:16:

AAGCTTCTAG AGGATCCTAT GTACGGTGGT TTCCTGACCT CCGAAAAATC TCAGACCCCG      60

CTGGTTACTC TGTTC                                                      75

(2) INFORMATION FOR SEQ ID NO:17:

(i) SEQUENCE CHARACTERISTICS:
            (A) LENGTH: 71 base pairs
            (B) TYPE: nucleic acid
            (C) STRANDEDNESS: single
            (D) TOPOLOGY: linear (ii) MOLECULE TYPE: DNA (genomic), LOWER STRAND (xi) SEQUENCE DESCRIPTION: SEQ ID NO:17:

```
GAGCTCGAAT TCGGATCCTC GCCTTTTTTG TATGCGTTTT TGATGATAGC GTTTTTGAAC        60

AGAGTAACCA G                                                             71

(2) INFORMATION FOR SEQ ID NO:18:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

AAGCTTCTAG AGGATCCTAT GTACGGTGGT TTCCTGACCT CCGAAAAATC TCAGACCCCG        60

CTGGTTACTC TGTTCAAAAA CGCTATCATC AAAAACGCAT ACAAAAAAGG CGAGGATCCG       120

AATTCGAGCT C                                                            131

(2) INFORMATION FOR SEQ ID NO:19:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

AAGCTTCTAG AGGATCCTAT GTACGGTGGT TTCCTGACCT CCGAAAAATC TCAGACCCCG        60

CTGGTTACTC TGTTC                                                         75

(2) INFORMATION FOR SEQ ID NO:20:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: DNA (genomic), LOWER STRAND (xi) SEQUENCE DESCRIPTION: SEQ ID NO:20:

GAGCTCGAAT TCGGATCCTT ATTCGCCTTT TTTGTATGCG TTTTTGATGA TAGCGTTTTT        60

GAACAGAGTA ACCAG                                                         75

(2) INFORMATION FOR SEQ ID NO:21:

(i) SEQUENCE CHARACTERISTICS:
        (A) LENGTH: 135 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

AAGCTTCTAG AGGATCCTAT GTACGGTGGT TTCCTGACCT CCGAAAAATC TCAGACCCCG        60

CTGGTTACTC TGTTCAAAAA CGCTATCATC AAAAACGCAT ACAAAAAAGG CGAATAAGGA       120

TCCGAATTCG AGCTC                                                        135
```

HYBRID POLYPEPTIDE COMPARING A BIOTINYLATED AVIDIN BINDING POLYPEPTIDE FUSED TO A POLYPEPTIDE OF INTEREST

FIELD OF THE INVENTION

This invention relates to a DNA expression vector for the production of a hybrid polypeptide. This invention also relates to a recombinant hybrid polypeptide comprising a polypeptide of interest fused to an avidin-binding polypeptide, said avidin-binding polypeptide containing a biotin attachment domain and a process for producing and recovering one or more polypeptides of interest.

BACKGROUND OF THE INVENTION

This invention relates to a DNA expression vector for the production of a hybrid polypeptide and particularly to a recombinant hybrid polypeptide composed of a polypeptide of interest fused to a polypeptide that contains a domain or recognition sequence for attachment of the prosthetic group biotin. More particularly, this invention relates to a hybrid polypeptide wherein the biotinylated hybrid polypeptide binds to avidin. This invention also describes a process for producing this hybrid polypeptide in a procaryotic or a eucaryotic protein expression system. Such a hybrid polypeptide can be obtained in high purity and yield using avidin monomer affinity chromatography (U.S. patent application Ser. No. 07/414,785, filed Sep. 29, 1989 and entitled HPLC AVIDIN MONOMER AFFINITY RESIN now U.S Pat. No. 5,276,062). U.S. Pat. No. 5,276,062 discloses a monomeric avidin polypeptide ligand and a novel and particularly efficacious process for isolating synthetic or natural molecules and/or biotinylated derivatives thereof, by adsorbtion of the molecules of interest onto a novel affinity media which contains avidin fixed to a solid inert support. The disclosure of Ser. No. 07/414,785 is incorporated herein by reference.

Synthesis of commercially important peptides and proteins has been limited by high production and purification costs and poor product recovery. Until recently, animals, microorganisms, plants, cadavers, serum, and urine have been the only sources from which bioactive polypeptides could be purified.

Biological synthesis of valuable polypeptides has been made possible in commercial quantities through advances in recombinant DNA technology. Recombinant DNA molecules directing the synthesis of commercially useful polypeptides can be introduced into procaryotic or eucaryotic expression systems. For example, recombinant DNA technology has enabled human growth hormone production by recombinant bacteria, and fermentation now replaces the traditional source. To date, biological synthesis is the only practical approach to the commercial-scale synthesis of peptides of greater than 20 amino acid residues.

Once synthesized, the desired polypeptide product must be purified from a complex mixture of cellular components. The degree of purification depends upon the intended application of the polypeptide. The cost of purification can account for up to 70% of the cost of production, as substantial losses of active ingredient usually occur during multistep purification processes.

Polypeptide purifications are usually achieved through one or more processes which are based upon physical properties of the polypeptide of interest. For example, proteins may be separated on the basis of solubility, size, ionic properties or affinity for specific ligands; usually several of these techniques are required to achieve acceptable purity.

Affinity resin chromatography can greatly reduce the number of purification steps required to achieve the desired level of purity. Affinity purification is based upon a specific binding interaction between a polypeptide to be purified and a ligand which is usually attached to a solid support. As used herein, the polypeptide binds to the ligand by virtue of a prosthetic group bound to an attachment domain present on the polypeptide. When a complex mixture such as a cell extract or crude mixture of synthetic peptides is passed over an affinity resin, the polypeptide to be purified is selectively retained by the resin and all molecules lacking the prosthetic group on the attachment domain are washed away from the resin. Therefore, in a single step, the polypeptide of interest may be recovered in high purity.

In order to use affinity chromatography to advantage for polypeptide purification, recombinant DNA technology can be used to construct chimeric gene fusions for recombinant hybrid polypeptides which in bacterial host cells incorporate the following elements: a 5' promoter; DNA coding for a polypeptide of interest; DNA coding for a polypeptide that contains a ligand binding domain; and optionally ribosomal terminators, such as the rrnB terminators found on the *E. coli* expression vector pkk223-3 (Brosius, J. and Holy A., *Proc Nat Acad Sci USA* 81:6929–6933 (1984); Brosius, J. et al *Plasmid* 6:112–118 (1984)). Suitable promoters are those which maximize expression of the desired gene in the host cell, and factors to be considered in promoter construction are discussed by Old and Primrose in Chapter 7 of *Principles of Gene Manipulation* 3rd Edition (Blackwell Scientific Publications, Palo Alto Calif. 1985). Examples of bacterial promoters appropriate for expression of cloned genes include the $P_L$, tac, lac, and trp promoters (ibid). The DNA used to construct chimeric gene fusions can be obtained from organisms or can be novel synthetic DNA fragments, or combinations thereof. The DNA sequences are assembled into a chimeric gene, which is inserted into a DNA expression vector in such a manner that in the appropriate host organism, the polypeptide of interest and the polypeptide for attachment to the affinity resin are produced as a single polypeptide chain.

In the present invention, a binding domain, or recognition sequence directs the attachment of a prosthetic group, such as biotin, to the hybrid polypeptide. The biotinylated hybrid polypeptide can be specifically selected by affinity ligand compositions such as the avidin monomer resin (U.S. patent application Ser. No. 414,785). A single purification step can therefore separate the protein of interest from complex mixtures, such as crude bacterial lysates, with high levels of recovery in a single chromatographic step, thus alleviating the recovery problems inherent to multistep purification processes. Such a combination of hybrid polypeptide and avidin monomer affinity resin would confer significant advantages to the purification of commercially useful polypeptides over existing processes.

Other systems for affinity purification of hybrid recombinant polypeptides have been described. However, significant technical obstacles limit their use for commercial-scale polypeptide purification. For example, chimeric genes encoding polypeptides containing a polyarginine C-terminal tail (Sassenfeld and Brewer, *Biotechnology* 2:76–81 (1984)) or polyhistidine domain (Smith et al. *J. Biol Chem* 263:7211 (1988)) can facilitate separation by ion exchange or metal chelate ion chromatography. Such systems are not broadly applicable because affinity interaction depends upon physical properties of the fusion polypeptide (chargeability to chelate metals), and it is not always possible to achieve sufficient change in these physical properties to permit affinity binding.

Another type of affinity chromatography is immunoaffinity chromatography, wherein polypeptides of interest are fused to immunogenic proteins such as *E. coli* beta-galactosidase (Ruther and Muller-Hill, *EMBO J* 2:1791–1794 (1983)) or small hydrophilic peptides (Hopp et al., U.S. Pat. No. 4,703,004 (1988)) to achieve purification. Polypeptides fused to staphylococcal protein A can be purified using IgG-Sepharose (Nilsson et al. *EMBO J.* 4:1075–1080 (1985), Lowenadler et al. *EMBO J.* 5:2393–2398 (1986)). Polypeptides fused to Protein G can be isolated using albumin as the immobilized ligand (Nygren et al. *J. Mol. Recognition*, 1:69 (1988)). A critical disadvantage limiting the usefulness of these methods is that extreme conditions, including the use of denaturants, are necessary to remove the fusion proteins from the affinity resin, which may destroy biological activity if native folding cannot be achieved. Low product recovery rates can also limit the usefulness of such systems.

Affinity based upon the binding of small molecules by a large protein is known as substrate-affinity chromatography. A small molecule, a ligand, forms a complex with a specific ligate. Examples of ligand:ligate combinations include avidin:biotin (Green in *Advances in Protein Chemistry* Vol 29 pp 85–133 Anson et al., Eds. (1975)), streptavidin:biotin (PCT/US85/01901, Meade and Garvin (1985)), lipoic acid:avidin (Green ibid), chloramphenicol acetyl transferase:acetyl CoA (EPO 0131363, Bennet et al. (1984)), beta-galactosidase: para-aminophenyl-beta-D-thio-galactoside (Offensberger et al. *Proc. Natl Acad. Sci USA* 82:7540–7544 (1985)), phosphate binding protein:hydroxyapatite (Anba et al. *Gene* 53:219 (1987)), maltose binding protein:starch (EPO 286239, Guan et al. 1988), and glutathione S-transferase:glutathione (Smith and Johnson *Gene* 67:21–30 (1988)).

In recent years, the unique properties of the prosthetic group biotin and its exceptionally high affinity ($10^{15}$ M$^{-1}$) and specificity for the proteins avidin and streptavidin (Green ibid.) have been exploited to devise powerful and widely applicable tools for microbiology, biochemistry and medical science (Wilchek and Bayer *Analyt Biochem* 171:1–32 (1988), Bayer and Wilchek *Methods in Biochem Anal* 26:1–45 (1980)).

Biotin (*Ann N.Y. Acad. Sci* 447:1–441, Dakshinamurti and Bhagavan, Eds. (1985)) is a prosthetic group found on only a few protein species. Attachment in vivo is mediated by biotin holoenzyme synthetases which recognizes a highly conserved attachment domain and catalyzes the covalent attachment of biotin to that domain (Wood et al, *J Biol Chem* 225:7397–7409 (1980); Shenoy and Wood, *FASCB S* 2:2396–2401 (1988)). Experiments using recombinant DNA technology have shown that biotin holoenzyme synthetases will biotinylate heterologous polypeptides containing this conserved attachment domain. For example, the 1.3S subunit of the enzyme transcarboxylase from Propionibacterium, which contains the conserved sequence, when cloned and expressed in *E. coli* is biotinylated by the *E. coli* synthetase (Murtif et al. *Proc Nat Acad Sci USA* 82:5617–5621 (1985)).

A polypeptide or part of a polypeptide containing the conserved biotin attachment domain, such as entire 1.3S (SEQ ID NO:1) protein or the biotin-binding recognition sequence identified within the 1.3S protein from Propionibacterium, (SEQ ID NO:2) can be incorporated into a hybrid recombinant polypeptide. Such a hybrid polypeptide containing a biotin attachment domain fused to one or more polypeptides of interest could be used to achieve the separation of virtually any recombinant protein based upon the affinity of the ligand avidin for the ligate biotin.

Avidin:biotin chromatography shares advantages generally applicable to substrate affinity chromatography systems for commercial-scale polypeptide purification. Substrate-affinity resins are generally inexpensive. Fusion proteins can be recovered using mild conditions by elution with free ligand. Post-translational addition of the biotin prosthetic group is independent of the final folded state of the protein (Wood et al. *J Biol Chem* 255:7397–7409 (1980)), an advantage when the host cell performs no post-translational modifications on the recombinant polypeptide. A ligand domain such as the domain directing biotin attachment would be particularly advantageous for recovery of fusion proteins found in inclusion bodies or for recovery of insoluble proteins which require denaturants or zwitterionic detergents for solubilization during extraction, prior to affinity chromatography.

Cronan (*J Biol Chem* 265:10327–10333 (1990)) has used a recombinant DNA plasmid from *E. coli* (Murtif et al. *Proc Nat Acad Sci USA* 82:5617–5621 (1985)) to construct fusion genes containing segments of the 1.3S gene, which contain the biotin attachment domain. Cronan (ibid) demonstrated that 1.3S sequences can be used to specifically label proteins in vivo, and to purify proteins from crude cell lysates by avidin affinity chromatography.

Cronan's (ibid) chimeric genes were constructed by fusing the 3' end of the genes of interest to the 5' end of the 1.3S gene, yielding hybrid recombinant polypeptide having the polypeptides of interest fused to the N-terminus of the 1.3S polypeptide. Such fusions are consistent with the teachings of Murtif and Samols (*J Biol Chem* 262:11813–11816 (1987)) who teach the fusion of the 3' end of the gene of interest to the 5' end of the 1.3S gene (the N-terminus of the 1.3S polypeptide) to avoid interfering with the attachment of biotin to its binding domain. Murtif and Samols (ibid) teach that the conformation of the COOH terminus of the 1.3 S polypeptide, and the spatial relationship between this region and a lysine residue positioned exactly 35 residues from the COOH terminus position to which biotin is attached in vivo, are essential for proper enzymatic recognition and biotinylation of the 1.3S polypeptide. Murtif and Samols (Ibid) further teach that the conformation of the carboxyl terminal region of the 1.3S polypeptide is critical for biotinylation, and that altering the hydrophobicity of the carboxyl terminal region of the 1.3S polypeptide "eliminates biotinylation." Murtif Samols did observe biotinylation of 1.3S polypeptides, each lengthened by two amino acids at the 1.3S carboxyl terminus. However, such additions of two amino acids to the C-terminus did not substantially change its hydrophobicity and such small additions would not be expected to change the conformation of the C-terminus. Therefore, Murtif and Samols (ibid) and Cronan (ibid) teach away from fusing the polypeptide of interest to the COOH terminus of the 1.3S polypeptides or fragments of the 1.3S polypeptide, so that the correct conformation of the biotin attachment region may be preserved.

It was therefore surprising to find that if one went against the teachings of Murtif and Samols (ibid) and Cronan (ibid) and fused a polypeptide of interest to the C-terminus of the 1.3S polypeptide, that the appropriate lysine residue of the 1.3S polypeptide within the hybrid was indeed biotinylated, since the addition of a polypeptide substantially longer than two amino acid residues would be expected from earlier teachings of Murtif and Samols to alter the conformation of the C terminus of the 1.3S polypeptide and preclude biotinylation. Additionally, hybrid polypeptides in which the 1.3S polypeptide was fused at its C-terminus to the polypeptide of interest were recovered in high purity and high yield in a single chromatographic step using Avidin Monomer Affinity chromatography (U.S. application Ser. No. 07/414, 785) now U.S. Pat. No. 5,276,062.

Further, an advantage is derived from fusing the polypeptide of interest to the C-terminus of the 1.3S polypeptide and not to its N-terminus. Protein expression level in a host cell is determined by a number of factors, including promoter strength and optimal initation of protein translation (ibid). Promoter strength contributes to the efficiency of transcription of messenger RNA. Optimization of the processes involved in the initiation of translation is important to achieving high levels of protein expression in the host cell. When polypeptides of interest are introduced at the 3' terminus of the 1.3S gene, no change is made to the optimal placement of the 5' terminus of the 1.3S gene directly adjacent to the promoter and 5' regulatory sequences. Insertion of the polypeptides of interest between the promoter and 5' terminus of the 1.3S gene may require additional expermination to achieve maximal expression levels in the host cell.

It is an object of this invention to provide a recombinant hybrid polypeptide comprising a polypeptide of interest fused to an avidin-binding polypeptide containing a domain for attachment of biotin, with that polypeptide of interest being fused to the avidin-binding polypeptide at the C-terminus of the avidin-binding polypeptide.

It is a further object of this invention to provide a DNA expression vector containing DNA sequences coding for a chimeric gene containing DNA sequences coding for a polypeptide of interest fused to DNA coding for a polypeptide containing a domain for attachment of biotin, with the DNA for the polypeptide of interest fused to the avidin-binding polypeptide at the 3' end of the DNA coding for the avidin-binding polypeptide.

It is a further object of this invention to provide a process for the production of a hybrid polypeptide of interest by constructing a plasmid for the hybrid polypeptide, transforming that plasmid into a procaryotic or eucaryotic host cell expression system, passing a hybrid polypeptide resulting from said expression system into contact with avidin and harvesting the resulting avidin-bound hybrid polypeptide of interest.

Other objects and advantages will become apparent from the following more complete description and claims.

BRIEF DESCRIPTION OF THE DRAWINGS

FIG. 2A shows an asp-pro cleavage site located between the C-terminus of the 1.3S polypeptide and the N-terminus of the β-endorphin polypeptide.

FIG. 2B shows an asp-pro cleavage site located between the C-terminus of the 1.3S polypeptide and the N-terminus of a novel reverse-endorphin polyeptide.

FIG. 2C shows a methionine cleavage site located between the C-terminus of the 1.3S polyeptide and the N-terminus of the β-endorphin polypeptide.

FIG. 3A shows the fusion of two contiguous β-endorphin polypeptides to the C-terminus of the 1.3S polypeptide from transcarboxylase of *Propionibacterium shermanii*.

FIG. 3B illustrates the fusion of a maltose binding protein to the N-terminus of the 1.3S polypeptide, and a synthetic β-endorphin is fused to the C-terminus of the same 1.3S polypeptide.

FIG. 3C shows the fusion of the moltose binding protein and a synthetic β-endorphin polypeptide, in tandem, to the N-terminus of the 1.3S polypeptide.

FIG. 4. Chimeric gene constructs for a hybrid polypeptide containing two noncontiguous polypeptides of interest, each fused to the C-terminus of noncontiguous polypeptides for attachment.

SUMMARY OF THE INVENTION

Figure 1:
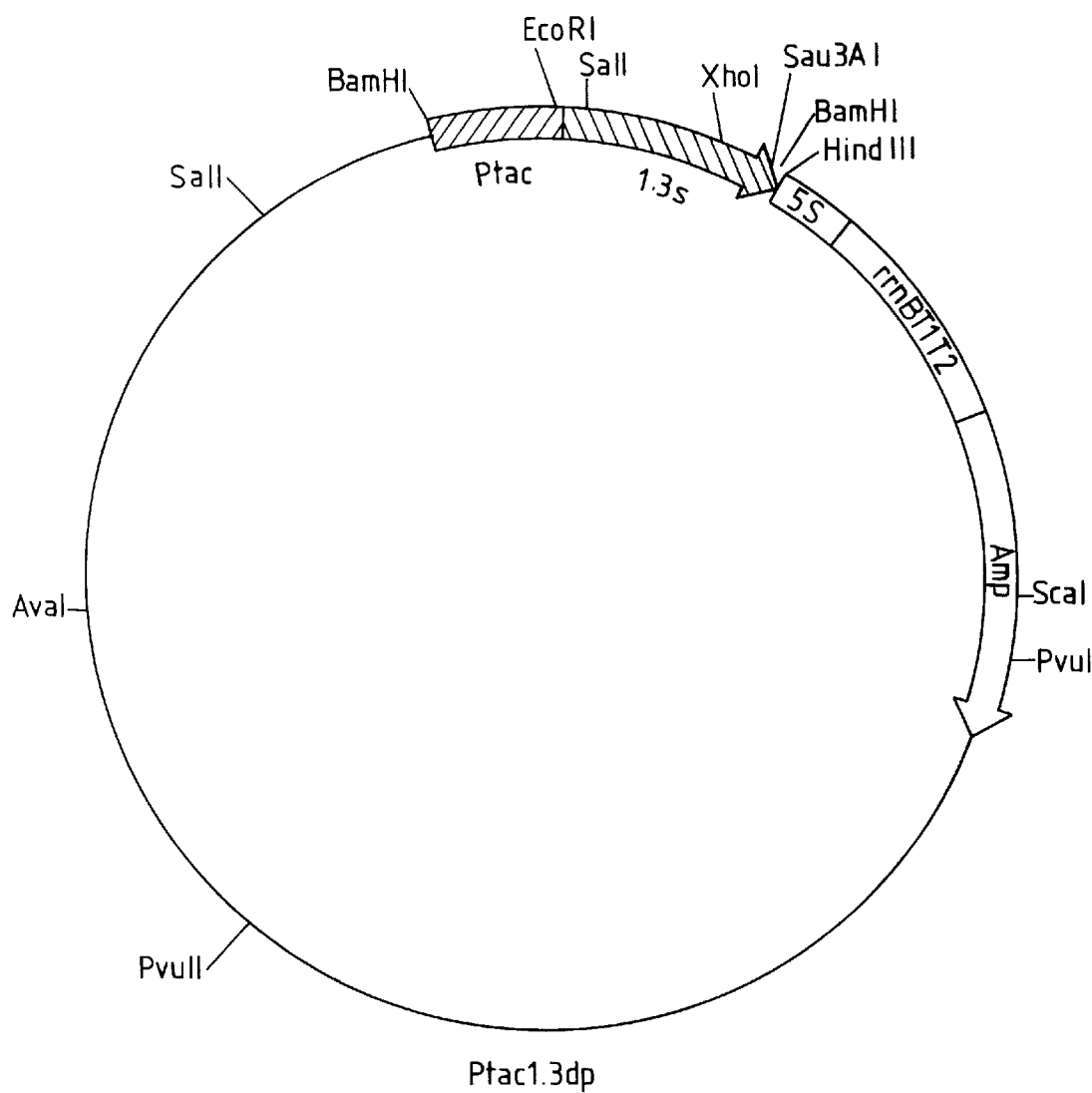
FIG. 1. Partial restriction map of plasmid ptac1.3dp.

Broadly this invention contemplates a composition of matter comprising a hybrid polypeptide for attachment of a biotin group for binding of a polypeptide of interest to avidin, said hybrid polypeptide comprising a biotinylated avidin-binding polypeptide and, fused to said avidin-binding polypeptide, at least one polypeptide of interest, said at least one polypeptide of interest being fused to said biotinylated avidin-binding polypeptide at the C-terminus of the avidin binding polypeptide.

This invention also contemplates a DNA expression vector containing in a 5' to 3' direction on the coding strand a gene comprising a 5' promoter region, a DNA sequence coding for a polypeptide for attachment of biotin for binding to avidin, and a DNA sequence coding for a polypeptide of interest.

This invention further contemplates a process for the production of a polypeptide of interest comprising forming a plasmid containing, in a 5' to 3' direction on the coding strand, a gene comprising a 5' promoter region, a DNA sequence coding for attachment of biotin for binding to avidin, a DNA sequence coding for a polypeptide of interest transforming said plasmid into a procaryotic or eucaryotic host cell expression system, passing a hybrid polypeptide resulting from said host cell expression system into contact with avidin, and harvesting the resulting avidin-bound hybrid polypeptide of interest.

DETAILED DESCRIPTION OF THE INVENTION

It is surprising to find that, contrary to the teachings of Cronan (ibid) and Murtif and Samols (ibid), when a polypeptide of interest is fused to the 1.3S polypeptide at the C-terminus of the 1.3S polypeptide, biotin is attached to the biotin-attachment domain of 1.3S polypeptide within this hybrid recombinant polypeptide. Cronan (ibid) and Murtif and Samols (ibid) teach that fusion at the C-terminus of the 1.3S may disrupt the native hydrophobicity and thus the native conformation of the 1.3S polypeptide, thus inhibiting biotinylation, and consequently inhibiting the binding of hybrid polypeptides to avidin. It is further surprising to find that the biotin prosthetic group attached to the 1.3S peptide fused at its C-terminus to another polypeptide is positioned so as to make the biotin molecule available for binding the hybrid polypeptide to the aforesaid avidin monomer affinity resin (U.S. Ser. No. 07/414,785) now U.S. Pat. No. 5,276, 062. The hybrid polypeptide is selectively retained by the avidin resin and can be recovered in high yield and high purity.

In accordance with the present invention, hybrid polypeptides comprising one or more polypeptides of interest and at least one polypeptide for attachment are produced by recombinant DNA methods. A cleavage amino acid or amino acids may be present. Such linking, or cleavage amino acids permit the seperation of polypeptides at a specific sit on the polypeptide when treated with the appropriate chemical reagent or enzyme. The cleavage site is positioned adjacent to the polypeptide of interest so that the polypeptide of interest may be cleaved from the polypeptide for attachment, if desired. The cloning vector is replicated and the hybrid polypeptide is produced in procaryotic or eucaryotic cells transformed by the vector. The hybrid polypeptide is purified away from the complex cell extract mixture by avidin affinity chromatography. A particularly preferred form of avidin is avidin monomer. An extract of transformed cells is made from cell culture or fermentation broth, the hybrid polypeptide rendered to a soluble state, and the extract is applied to the avidin monomer column. The column is washed with adequate amounts of a wash buffer to clear the column of unbound materials. The hybrid polypeptide is eluted from the column. After the hybrid polypeptide is eluted from the column, the polypeptide for attachment may optionally be cleaved from the polypeptide of interest with the appropriate cleavage reagent or enzyme. Passage of the cleaved mixture over the avidin monomer column yields a highly purified preparation of the polypeptide of interest, and the polypeptide for attachment is retained by the column.

Referring to FIG. 1, a partial restriction map of plasmid ptac1.3dp is shown. ptac1.3dp was created by modification of plasmids ptac1.3t and ptac1.3(1–125) obtained from D. Samols, Case Western Reserve University.

E. Coli strain CSH26 containing the plasmid ptac1.3dp was deposited on Mar. 19, 1992, in the American Type Culture Collection, 10801 University Boulevard, Manassas, Va. 20110-2209. This deposit was made pursuant to the Budapest Treaty On The International Recognition Of The Deposit Of Microorganisms For The Purposes Of Patent Procedure.

Figure 2:
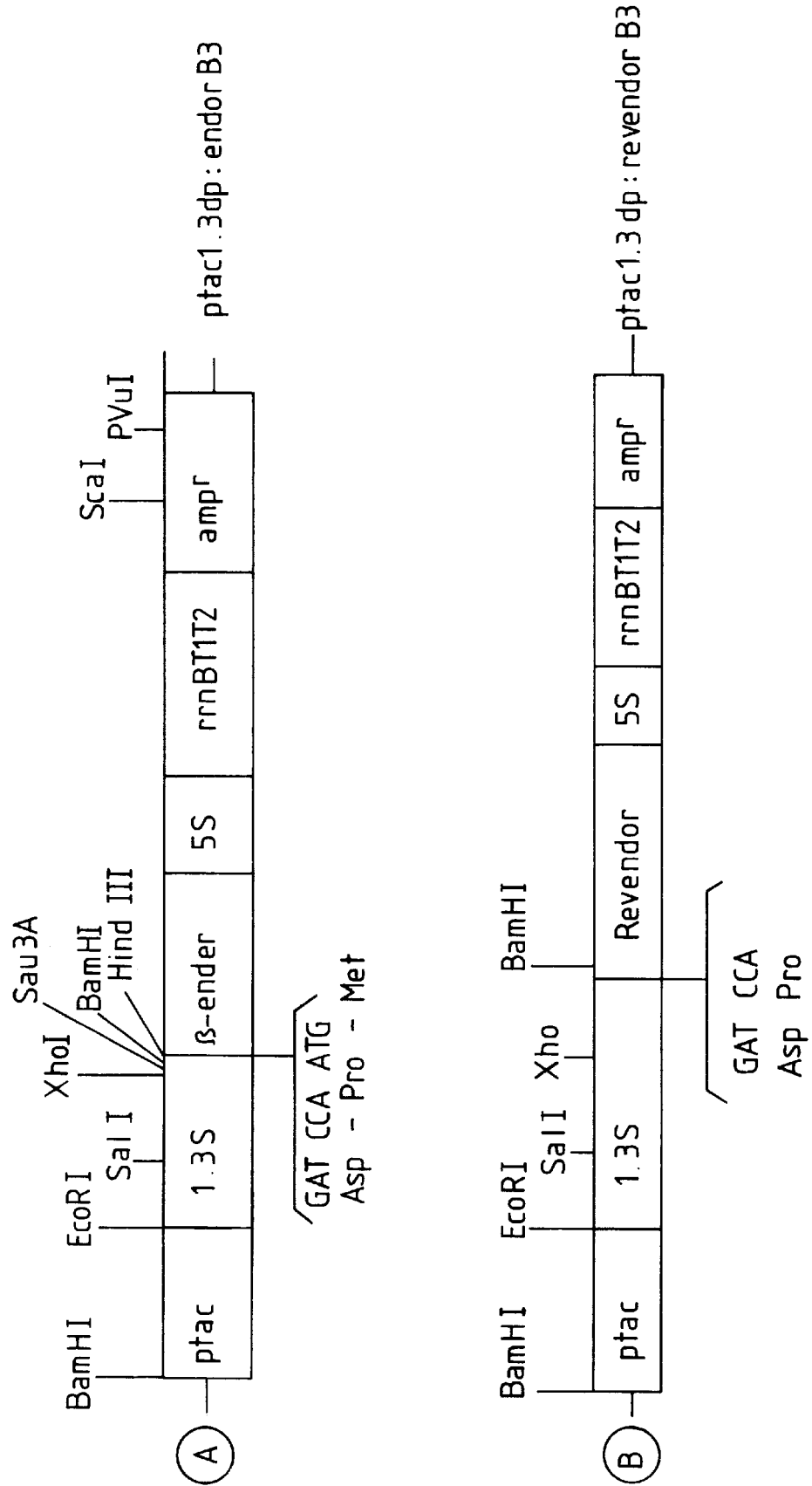
FIG. 2A–2C. Chimeric gene constructs for hybrid polypeptides constructed so that the polypeptide of interest is fused at the C-terminus of the polypeptide for attachment.
FIG. 2D shows no cleavage site located between the C-terminus of the 1.3S polyeptide and the N-terminus of the β-endorphin polypeptide.

Referring to FIG. 2, chimeric gene constructs for hybrid polypeptides are shown. The chimeric genes are constructed so that the polypeptide of interest is fused at the C-terminus of the polypeptide for attachment. In these examples, the polypeptide of interest is a synthetic β-endorphin, and the polypeptide for attachment is the 1.3S polypeptide from transcarboxylase of Propionibacterium shermanii. In FIG. 2A is shown an asp-pro cleavage site located between the C-terminus of the 1.3S polypeptide and the N-terminus of the β-endorphin polypeptide. In FIG. 2B is shown an asp-pro cleavage site located between the C-terminus of the 1.3S polypeptide and the N-terminus of a novel reverse-endorphin polypeptide. In FIG. 2C is shown a methionine cleavage site located between the C-terminus of the 1.3S polypeptide and the N-terminus of the β-endorphin polypeptide. In FIG. 2D, no cleavage site is located between the C-terminus of the 1.3S polypeptide and the N-terminus of the β-endorphin polypeptide.

Figure 3:
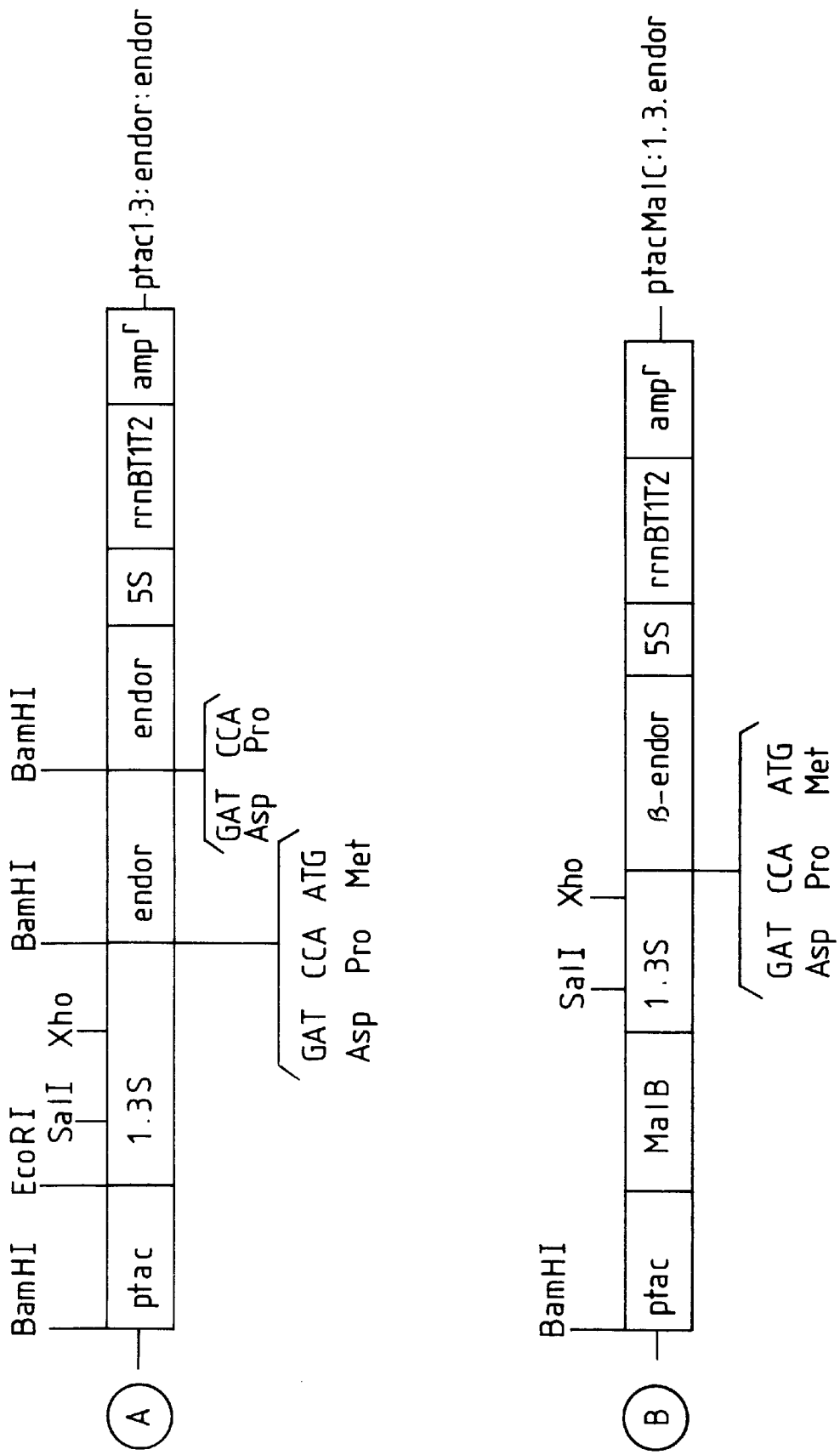
FIG. 3A–3C. Chimeric genes for hybrid polypeptides containing more than one polypeptide of interest fused to a single polypeptide for attachment.

Referring to FIG. 3, chimeric genes for hybrid polypeptides are illustrated which contain more than one polypeptide of interest fused to a single polypeptide for attachment. In FIG. 3A is shown the fusion of two contiguous β-endorphin polypeptides to the C-terminus of the 1.3S polypeptide from transcarboxylase of Propionibacterium shermanii. In FIG. 3B is illustrated the fusion of two different noncontiguous polypeptides of interest to the 1.3S polypeptide. A maltose binding protein is fused to the N-terminus of the 1.3S polypeptide, and a synthetic β-endorphin is fused to the C-terminus of the same 1.3S polypeptide. FIG. 3C shows the fusion of two different contiguous polypeptides of interest to the N-terminus of the 1.3S polypeptide. The maltose binding protein and a synthetic β-endorphin polypeptide are fused in tandem to the N-terminus of the 1.3S polypeptide.

Referring to FIG. 4, chimeric gene constructs for a hybrid polypeptide containing two noncontiguous polypeptides of interest are shown. Each coding sequence is fused to the C-terminus of a noncontiguous polypeptides for attachment. In the specific example, two synthetic β-endorphin polypeptides are each fused to the C-terminus of a different 1.3S polypeptide.

Polypeptide of Interest

The polypeptide of interest can comprise substantially any procaryotic or eucaryotic polypeptide that can be expressed by a vector in a host cell. Among the polypeptides of interest which may be produced by such means are enzymes, such as proteases, oxidoreductases, transferases, hydrolases, lyases, isomerases, ligases, or the like.

The present invention also contemplates the production of storage polypeptides, such as ferritin or ovalbumin or transport polypeptides, such as hemoglobin, serum albumin, eruloplasmin, or the like. Also included are the types of polypeptides that function in contractile and motile systems, for example actin and myosin or the like.

The present invention also contemplates the production of polypeptides that serve a protective or defense function, such as the blood polypeptides thrombin and fibrinogen. Other protective polypeptides include the binding polypeptides, such as antibodies or immunoglobulins that bind to and thus neutralize antigens. Additionally this invention contemplates Protein A, or the like.

The polypeptide produced by the present invention also may encompass various hormones such as endorphins, human growth hormone, somatostatin, prolactin, estrogen, progesterone, thryotropin, calcitonin, gonadotropin, insulin or the like. Other such hormones include those that have been identified as being involved in the immune system, such as interleukin 1, interleukin 2, colony stimulating factor, macrophage-activating factor, interferon, or the like.

The present invention may be used to produce toxic polypeptides, such as ricin from castor bean or gossypin from cotton seed, and the like.

Polypeptides that serve as structural elements may be produced by the present invention, such polypeptides include the fibrous polypeptides collagen, elastin and alpha-keratin. Other structural polypeptides include glycoproteins, virus-proteins, muco-proteins and the like.

Polypeptides that may be utilized as diagnostic agents, for example as markers for the presence of certain diseases, are also contemplated by this invention.

Additional polypeptides of interest that may be produced as hybrid polypeptides are polypeptides that may be used for therapeutic purposes, for example polypeptides with anti-tumor activity, polypeptides useful in vaccine production, polypeptides having amino acid sequences for recognition of antigens, or polypeptides which can function as diagnostic reagents, and the like.

In addition to the above-noted naturally occurring polypeptides, the present invention may be used to produce synthetic polypeptides, defined generally as any sequence of amino acids not occurring in nature.

Polypeptide for Attachment

An avidin-binding polypeptide for attachment is generally a polypeptide that enables the attachment of a hybrid fusion polypeptide to avidin. Among such polypeptides for attachment that may be used are those containing a recognition sequence for attachment of the prosthetic group biotin, such as the 1.3S polypeptide subunit of transcarboxylase from Propionibacterium.

In addition to using the entire sequence of the 1.3S polypeptide as the polypeptide for attachment, other smaller portions of the 1.3S polypeptide may be used which direct the attachment of biotin, particularly portions comprising all or part of amino acid residues 58 through 100 (SEQ ID NO: 2). One or more deletions, substitutions, insertions or mutations may be made by methods well known in the art which result in a biotinylated 1.3S polypeptide or biotinylated fragment. The nucleotide sequence coding for the 1.3S polypeptide or fragments may be synthesized using a commercially available DNA synthesizer in a manner well known in the art.

Additionally, other polypeptides or portions thereof that are enzymaticaly biotinylated may also be employed without departing from the spirit or scope of this invention.

Arrangement of the Hybrid Polypeptide

The hybrid polypeptide comprises at least one polypeptide for attachment fused to at least one polypeptide of interest. It is preferred that at least one polypeptide of interest be fused to the C-terminus of the polypeptide for attachment. Optionally, a plurality of polypeptides of interest may be fused sequentially at the C-terminus of the polypeptide for attachment. Or, a plurality of contiguous polypeptides of interest may be fused sequentially at the N-terminus of the polypeptide for attachment. Additionally, more than one polypeptide of interest may be present in a noncontiguous arrangement, for example, one polypeptide of interest may be fused to the N-terminus of the polypeptide for attachment and one polypeptide fused at the C-terminus of the same polypeptide for attachment. Two polypeptides of interest may be fused to the C-termini of two polypeptides for attachment arranged as polypeptide for attachment 1: polypeptide of interest 1: polypeptide for attachment 2: polypeptide of interest 2. In any of the arrangements disclosed here, the polypeptides of interest may be the same, or different. The polypeptides for attachment may be the same, or different.

An advantage of fusing a plurality of polypeptides of interest to at least one polypeptide for attachment is the ability to increase the yield of a single polypeptide of interest present by including two copies of that polypeptide within a single hybrid polypeptide, or to increase the number of polypeptide species that can be purified simultaneously by a single avidin affinity chromatography step, if the polypeptides of interest are different.

The hybrid polypeptide may contain a linking amino acid or amino acids for cleaving the polypeptide or polypeptides of interest from the polypeptide or polypeptides for attachment. The linking amino acid or amino acids are incorporated between the polypeptide or polypeptides for attachment and the polypeptide or polypeptides of interest in such a way that one or more cleavage reactions separate each polypeptide species to the degree necessary for intended applications. It may not in every instance be necessary to cleave all, some, or any of the species within a particular hybrid polypeptide.

Amino acids that may be used to link the polypeptide of interest to the polypeptide for attachment include aspartic acid-proline, asparagine-glycine, methionine, cysteine, lysine-proline, arginine-proline, isoleucine-glutamic acid-glycine-arginine, and the like. The at least one polypeptide for attachment may be cleaved from the at least one polypeptide of interest by exposure to the appropriate chemical reagent or cleaving enzyme.

It should be recognized that cleavage of the polypeptide or polypeptides of interest from the polypeptide or polypeptides for attachment may not be necessary for every hybrid fusion polypeptide that is constructed, in which case a cleavage site could be incorporated, or absent.

The avidin used to bind the biotin attached to the hybrid polypeptide may be monomeric or tetrameric avidin, or streptavidin. Avidin monomer is the preferred form of avidin affinity medium. Advantages of using avidin monomer to separate the polypeptide of interest from crude cell mixtures include reversible binding of the polypeptide for attachment to avidin, high yield, and high purity of the desired polypeptide of interest following affinity chromatography.

Assembly and Expression of Genes for Hybrid Polypeptides

Genes coding for hybrid polypeptides may be produced by recombinant DNA methods by combining within a DNA expression vector a chimeric gene comprising a 5' promoter region, DNA sequences coding for at least one polypeptide for attachment of a prosthetic group for binding to avidin, and at least one DNA sequence coding for a polypeptide of interest. Optionally, the chimeric gene may contain at least one DNA sequence coding for a linking amino acid or amino acids, that is, one or more amino acids for cleaving a polypeptide of interest from a polypeptide for attachment.

Genes coding for the various types of polypeptides of interest, for example those identified above, may be obtained from a variety of procaryotic or eucaryotic sources, such as plant or animal cells or bacterial cells. Genes can be isolated from chromosomal material of eucaryotic or procaryotic cells, or from plasmids or viruses of procaryotic or eucaryotic cells by employing standard, well-known techniques. Additionally, automated DNA synthesis may be used to obtain DNA coding for naturally-occurring or synthetic polypeptides. To enable chimeric gene expression in host cells, a variety of naturally-occurring and synthesized DNA expression vectors having genes coding for many different polypeptide molecules are now commercially available from a variety of sources. The desired DNA can also be produced from mRNA by using the enzyme reverse transcriptase. This enzyme permits the synthesis of DNA from an RNA template.

In accordance with the present invention, once genes coding for one or more desired polypeptides of interest are isolated, synthesized or otherwise obtained, said gene or genes are joined to at least one gene coding for a polypeptide containing a recognition sequence for attachment of the prosthetic group biotin, thus enabling the attachment of the hybrid polypeptide to avidin.

A gene directing the synthesis of a polypeptide for attachment is generally one coding for a polypeptide that enables the binding of a hybrid fusion polypeptide to avidin. Among such genes coding for polypeptides for attachment that may be used are those coding for amino acid sequences that direct the attachment of the prosthetic group biotin, for example the gene for the 1.3S polypeptide subunit of transcarboxylase from Propionibacterium.

A gene coding for a polypeptide for attachment may be one that directs the attachment of the prosthetic group biotin. A particularly biotinylated preferred biotinylated polypeptide for attachment is the 1.3S subunit of transcarboxylase from *Propionibacterium shermanii* (SEQ ID NO:1). Although the gene coding for the entire 1.3S polypeptide from *Propionibacterium shermanii* is preferred(SEQ ID NO: 4), optionally any gene or gene fragment coding for a polypeptide that directs the attachment of biotin may be suitable. The preparation of gene fragments is well known to those skilled in the art.

The gene or genes coding for the at least one polypeptide of interest and the gene or genes coding for the polypeptide or polypeptides for attachment are preferably treated with the appropriate restriction enzymes, or otherwise treated to have cohesive termini to facilitate ligation with other elements of the chimeric gene or the DNA expression vector.

The resulting DNA expression vector carrying the chimeric hybrid polypeptide gene is used to transform the appropriate procaryotic or eucaryotic host cell. The selection of a DNA expression vector appropriate for the desired host cell is well known to those skilled in the art. Following the transformation procedure, the transformed host cells are isolated and analyzed for expression of the hybrid polypeptide. Those transformants identified as containing the hybrid polypeptide are further analyzed by restriction enzyme digestion, DNA sequencing and other methods for confirming the correctness of the desired gene, by methods well known to those skilled in the art.

The transformants identified as host cells carrying the gene for the desired hybrid polypeptide are then multiplied in culture to cause replication of the vector and high-level expression of the hybrid polypeptide that contains the polypeptide of interest. The cloning vector may be used to additionally transform other strains of compatible hosts for large-scale production of the hybrid polypeptide.

Various methods used for obtaining genes or gene fragments, preparing DNA expression vectors, transforming host cells, expressing hybrid polypeptides in host cells, and identifying those polypeptides are set forth by J. Sambrook, E. F. Fritsch, and T. Maniatis, *Molecular Cloning, 2nd Edition*. Cold Spring Harbor Press, 1989, and also by F. M. Ausubel, R. Brent, R. E. Kingston, D. M. Moore, J. G. Seidman, J. A. Smith, K. Struhl., Eds. *Current Protocols in Molecular Biology*, Volume 1. John Wiley and Sons, New York 1989, which disclosure is incorporated herein by reference.

Preparation of DNA Expression Vectors

To prepare DNA expression vectors, various cloning vectors may be used. A plasmid is preferred, however, a cosmid or bacteriophage may be used. If insect, plant, or mammalian cells are used as host cells, viruses may also be used as vectors. DNA expression vectors may be obtained from natural sources or may comprise synthetic DNA. The plasmid chosen for a particular expression system should be compatible with that host, to ensure vector replication and polypeptide expression. The plasmid chosen for incorporation of the genes coding for the hybrid polypeptide should possess an origin of replication recognized by the host cell.

The DNA expression vector should contain DNA sequences recognized by restriction endonuclease enzymes to cleave the vector for subsequent ligation with the gene for the hybrid polypeptide without inactivating the origin of replication or functions necessary for plasmid selection following transformation, for example within an antibiotic resistance gene. The vector should contain restriction enzyme cleavage sites that provide suitable termini for joining and ligation of foreign genes to be inserted. Preferably, the DNA vector contains a single site or two unique sites for incorporation of the hybrid polypeptide gene, neither of which occurs within that gene. To accommodate more than one different foreign gene possibly terminating in different cohesive or blunt termini, it would be useful for the vector to possess a large number of unique restriction enzyme cleavage sites.

The DNA expression vector should cause a phenotype to be expressed that will enable transformed cells to be readily identified and separated from cells which do not undergo transformation. Such phenotypic selection genes can include genes providing resistance to a particular antibiotic, which inhibits growth of untransformed but not transformed cells. Such genes are widely available now and confer resistance to antibiotics such as ampicillin, tetracycline, streptomycin, kanamycin, and the like. Plasmids which contain an inserted gene that disrupts the B-galactosidase gene, such as the hybrid polypeptide gene, can be identified following transformation by the inability of the host cell to reduce reagent 5-bromo-4-chloro-3 indolyl-$\beta$-D-galactopyranoside (X-gal) in the media and cause the bacterial colony to develop a blue coloration. Such plasmids, reagents, and media are known to those skilled in the art.

Preferably, *E. coli* is employed as the host cell, and a plasmid is preferred for cloning and transformation of the *E. coli* host. The preferred plasmid is pKK223-2(Pharmacia, Uppsala, Sweden). This plasmid carries genes for an origin of replication in *E. coli*, and a gene for resistance to the antibiotic ampicillin. This plasmid also has a synthetic linker region consisting of unique restriction endonuclease cleavage sites to facilitate cloning. This plasmid contains the strong tac promoter, which directs high levels of transcription in *E. coli*.

If insect cell culture is to be used for production of hybrid polypeptide, the preferred plasmid is pVL1392 (obtained from M. Summers, University of Texas, available commercially from Invitrogen, Inc. San Diego Calif.). An advantage of insect cell culture is that polypeptides requiring glycosylation or other types of post translational modfications including folding with appropriate disulfide bond formation may be so modified in an insect cell expression system, whereas this manner of post-translational modification is not performed by procaryotic hosts.

To prepare the chosen plasmid for insertion of the chimeric gene comprising the hybrid polypeptide gene, the plasmid is digested with restriction endonucleases, for example BamHI or EcoRI, or any restriction enzyme or enzyme combination that cleaves the plasmid at a unique site and produces cohesive 3' and 5' termini complementary to termini of the chimeric gene to be ligated. If desired, the plasmid may be treated with two different enzymes to produce two different cohesive termini to facilitate ligation of the chimeric hybrid polypeptide gene or genes in the correct orientation within the plasmid. Certain enzymes which produce blunt ends may also be used, or linker molecules may be added to vector or foreign genes to prepare the desired cohesive termini. Such strategies and methods are well known to those skilled in the art.

When the plasmid is digested, two or more DNA fragments may be generated. The desired plasmid fragment carrying the origin of replication and other genes essential to replication and identification of the plasmid may be identified and recovered by gel electrophoresis and other techniques well known in the art.

Preparation of the Gene for the Polypeptide for Attachment

A particularly preferred arrangement for the members of the hybrid polypeptide is the location of the polypeptide for attachment, most preferably the 1.3S polypeptide directly 3' to the promoter at the PstI site within the synthetic linker of the plasmid pkk223-3. The PstI site is 3' to the promoter and to a ribosome binding site.

It should be understood that any deletions, insertions, substitutions, or mutations which may be performed on the 1.3S gene which still direct the attachment of biotin are contemplated within the spirit and scope of this invention. Additionally, other genes or gene fragments, natural or synthetic, whose resulting polypeptides direct the attachment of biotin or lipoic acid fall within the scope and spirit of this invention.

The 1.3S gene is preferably constructed with a cleavage site for PstI at its 5' terminus and a cleavage site for BamHI at its 3' terminus, such that upon ligation, the 1.3S gene is connected in the proper reading frame with the tac promoter, a ribosome binding site is intact, and the 1.3S gene or fragment preferably terminates in the nucleotide sequence GAT CCA TAA CGC CTA AGC TT (SEQ ID NO: 3), or any such sequence which simultaneously provides a BamHI restriction endonuclease cleavage site and codes for the amino acids asp-pro. Asp pro is the preferred sequence used as linking amino acids the cleavage of the 1.3S polypeptide for attachment from appropriate polypeptides of interest. However, if a polypeptide of interest contains within its sequence one or more asp-pro sequences, then optionally any other linking amino acid or amino acids not present in the polypeptide of interest may be substituted for asp-pro. It will be necessary to structure the gene in such instances that appropriate cohesive termini are created that permit ligation of the 1.3S gene to the gene for the polypeptide of interest.

The gene or genes for the at least one polypeptide of interest may be isolated, synthesized, or otherwise obtained and modified at the 5' terminus so that ligation to the appropriate terminus of the gene for the polypeptide for attachment is facilitated. The 3' terminus of the 1.3S polypeptide for attachment is the preferred terminus for ligation of the gene for the polypeptide of interest, in the proper reading frame. Furthermore, the 3' terminus of the last polypeptide of interest in sequence in the chimeric gene should preferably be prepared so that this terminus is complementary to the 5' terminus of the plasmid vector, to facilitate ligation to the expression vector.

It is to be understood that for different chimeric genes, obtaining the correct orientation of the polypeptide or polypeptides of interest relative to each other and to the polypeptide or polypeptides for attachment within the expression vector employ the basic steps as outlined above. Preferably, the gene for each polypeptide of interest is attached in the proper reading frame to the adjacent gene, and all adjacent termini are prepared in a manner so as to make them complementary to facilitate ligation. Furthermore, genes for any polypeptides of interest requiring cleavage from another polypeptide of interest or from one or more polypeptides for attachment must be so constructed as to allow for the proper positioning of all cleavage sites so that their insertion does not result in any genes for any of the polypeptides being in an improper reading frame.

The ligation reaction, which covalently joins fragments of DNA, is described in Sambrook, Fritsch, and Maniatis (ibid), and Ausubel et al. (ibid) and is well known to those skilled in the art.

The ligated plasmid is ready for transformation of host cells. The preferred host is *E. coli*, however, other bacteria, insect cells, yeast, or mammalian or plant cells may be used with a DNA expression vector appropriate to that particular host cell.

Transformation of *E. coli* is a standard procedure well known to those skilled in the art, wherein a suitable host strain, such as *E. coli* HB101 accepts, harbors, replicates and expresses the plasmid carrying the gene for the hybrid polypeptide. Transformation of *E. coli* is described by Sambrook, et al. If the host is an insect cell, transfection may be accomplished by a procedure such as that described by M. Summers and G. Smith, *A Manual of Methods for Baculovirus Vectors and Insect Cell Culture Procedures*. Texas Agricultural Experiment Station Bulletin No. 155, 1988.

In order to identify the host cells which are transformed, the culture is placed in selective media containing an appropriate antibiotic. Only those cells with plasmid-borne resistance will survive. Plasmid can be recovered after lysis of surviving cell colonies, and characterized by restriction enzyme digestion and mapping, DNA sequencing, or other methods known in the art. Additionally, those colonies which express hybrid polypeptide can be identified by immunological assay, such as ELISA or Western blotting. In some embodiments it may be possible to assay directly for biological activity of the polypeptide or polypeptides of interest.

Once transformed cells carrying the hybrid polypeptide are identified, they may be multiplied by established techniques, such as fermentation. In addition, the recovered plasmids can be used to transform other strains of bacteria, or appropriate hosts cells for large-scale production and expression of the hybrid polypeptide.

Purification of the Hybrid Polypeptide

The hybrid polypeptide which contains the polypeptide for attachment, the biotin group for binding to avidin, the polypeptide of interest, and the optional cleavage site, expressed by the transformed host cells is separated from the medium and other debris by affinity chromatography. The preferred affinity medium is avidin monomer resin (U.S. Ser. No. 414,785). To this end, host cells are separated from the medium and broken open for example, by sonication. Optionally, hybrid polypeptides can be excreted into the culture media if a signal peptide for extracellular secretion is included at the appropriate terminus of the hybrid polypeptide. Should such a secreted polypeptide be desired, it may be necessary to include a DNA sequence coding for a polypeptide directing extracellular secretion within the chimeric gene coding for the hybrid polypeptide.

The hybrid polypeptide once released is maintained in an appropriate buffer, preferably one in which it is soluble. The buffer solution should be formulated to maximize hybrid polypeptide recovery from host cells. Buffer properties which may be optimized to favor recovery include but are not limited to, pH, ionic composition, ionic strength, or presence or absence of various detergent compositions.

Optionally some fractionation of the host cell extract may be performed in order to concentrate or partially purify the hybrid polypeptide prior to affinity chromatography. One preferred method is ammonium sulfate fractionation. It is to be understood that other methods commonly employed in protein purification may also be used prior to affinity chromatography. The cell extract is passed over the preferred column for affinity chromatography, the avidin monomer column, which is then washed extensively with buffer to remove all unbound materials. The hybrid polypeptide is specifically eluted from the column, preferably with acetic acid or biotin. As as result, a high yield of highly purified hybrid polypeptide containing the polypeptide of interest is obtained.

Separation of the Polypeptide for Attachment From the Polypeptide of Interest

It may be desirable or necessary to cleave the one or more polypeptide of interest from the one or more polypeptide for attachment to restore biological activity to the polypeptide of interest. Separation from the polypeptide for attachment may be accomplished by first suspending the hybrid polypeptide in buffer. Thereafter the chemical or proteolytic cleavage agent specific to the linking amino acid or amino acids is added to the suspension and the polypeptide of interest is cleaved. For example, if the polypeptide of interest is linked to the polypeptide for attachment by an asp-pro linkage, a volatile acid such as formic acid may be added to the suspension to effect cleavage. If methionine is the linking amino acid, the reagent cyanogen bromide may be used to cleave between methionine and the first amino acid of the polypeptide of interest.

A volatile cleavage reagent, such as formic acid or cyanogen bromide, may be evaporated away from the polypeptide mixture. If cleavage is accomplished by an enzyme, the enzyme may be removed from the mixture by passing the mixture through an enzyme substrate column. If it is necessary to obtain the polypeptide of interest pure from the polypeptide for attachment, this removal may be accomplished by passing the mixture through an avidin affinity column. In this way, the polypeptide for attachment, by binding to the avidin, will be retained and therefore separated from the highly purified solution of the polypeptide of interest, which will not bind to avidin.

It should be noted that some polypeptides of interest will assume their desired biological activity with the polypeptide for attachment still attached. As a consequence, the polypeptide for attachment will not need to be cleaved from the polypeptide of interest and the steps described to separate the polypeptide of interest and the polypeptide for attachment need not be performed. Moreover, in circumstances where the polypeptide for attachment remains attached to the polypeptide of interest, linking amino acid or amino acids may be present or omitted. In this situation, the construction and method of preparing the DNA expression vectors, detailed above, can be appropriately modified.

General Procedures

The following examples are carried out using one or more of the general procedures set forth below. In all of the following examples, restriction endonucleases, ligases, polymerases, and other DNA modifying enzymes described in specific experimental steps are used according to the recommendations of the manufacturer of the particular enzyme or reagent used. Two laboratory manuals, *Current Protocols in Molecular Biology* (Ausubel et al 1989)), and *Molecular Cloning A Laboratory Manual 2nd Edition* (Sambrook et al, Cold Spring Harbor Press, Cold Spring Harbor, N.Y. (1989)) referenced below, contain supplemental information that may also be useful to one skilled in the art in conducting the examples described below.

Procedure I. Restriction Endonuclease Digestion of DNA

Restriction endonuclease digestions using one or more restriction enzymes to digest DNA are generally carried out using the protocols set forth in Ausubel et al. *Current Protocols in Molecular Biology Volume* 1, Chapter 3, Unit 3.1. Restriction mapping of plasmids is generally carried out using the protocols set forth in Ausubel et al (ibid), Unit 3.2. Restriction enzymes are obtained from Promega (Madison Wis.) or New England Biolabs (Beverly Mass.) and complete or partial digestion of DNA with specific enzymes are performed generally according to the manufacturer's recommendations.

Procedure II. Purification of DNA Fragments Using Agarose Gel Electorphoresis

Agarose gel electrophoresis is generally carried out using the protocols set forth in Ausubel et al (ibid), Volume I, Chapter 2, Unit 2.5A. Separation and isolation of larger (>1 kb) DNA fragments from excised gel fragments is generally carried out as set forth by Ausubel et al (ibid), Chapter 2, Unit 2.6, and separation and isolation of smaller (<1 kb) DNA fragments is carried out as set forth in Ausubel et al (ibid) Chapter 2, Unit 2.7. Removal of salts and gel fragments from larger DNA fragments is accomplished using the GeneClean kit (Bio101, Inc. San Diego, Calif.) using procedures supplied by the manufacturer, and removal of salts and gel fragments from smaller DNA fragments is accomplished using the MerMaid kit (Bio101, Inc. San Diego, Calif.) also using the procedures recommended by the manufacturer.

Procedure III. Ligation of DNA Fragments

Ligation of DNA fragments using T4 DNA Ligase (New England Biolabs Beverly Mass.) is generally carried out as in Ausubel et al (ibid), Unit 3.14, using conditions recommended by the manufacturer.

Procedure IV. Preparation of Competent *E. coli* Cells and Transformation of *E. coli*

Preparation of competent *E. coli* CSH26 cells using calcium chloride and transformation with DNA expression vectors are carried out using the protocols described by Sambrook et al *Molecular Cloning A Laboratory Manual 2nd Edition* 1989, Chapter 1. Clones carrying plasmids containing DNA insertions are identified by growing cells on L-agar supplemented with 100 mg/L ampicillin.

Procedure V. Isolation of Plasmid DNA

Plasmid DNA is generally isolated using the protocols set forth by Ausubel et al (ibid) Chapter 1, Unit 1.7.

Procedure VI. Preparation of Double-stranded DNA from Synthetic Single-stranded Oligonucleotides Oligonudeotides are synthesized using standard phosporamidite chemistry (0.2 micromole synthesis). Fragments are separated on a 20% polyacrylamide gel under denaturing conditions as described by Ausubel et al (ibid) Volume 1, Unit 2.12 and eluted and desalted as described therein. Double-stranded DNA is assembled from upper strand and lower strand pairs of synthetic oligonucleotides with overlapping regions of perfect complimentarity of 15 nucleotides at their 3' ends by heating a mixture of 1 ug of each of the strands at 90° C. for 5 minutes, followed by slow cooling to room temperature over a period of one to two hours. This short duplex region serves as template and primer for mutually primed synthesis of a complete double DNA strand with Sequenase, a T7 DNA polymerase obtained from US Biochemical, using protocols supplied by the manufacturer. Following duplex extension, the DNA double strand is purified by agarose gel electrophoresis as described in Procedure II.

Procedure VII. Preparation of Crude *E. coli* Cell Extract

*E. Coli* host cells harboring the plasmid carrying the gene for the hybrid polypeptide are grown to stationary phase by overnight incubation in L-broth containing 100 mg/L ampicillin at 42° C., 250 RPM in a New Brunswick incubator-shaker. Cells are collected by centrifugation in a GSA rotor at 5,000×G for 30 minutes at 4° C. in a Sorvall RC-5B centrifuge to pellet the cells. The supernatant is poured off, and the cell pellet is weighed. The cells are resuspended in 1:2 (cell wet weight: buffer volume) 100 mM potassium phosphate buffer, pH 6.8–7.2 (or appropriate buffer at pH 4.0 to 11.0), at 4° C. The cells are then lysed by sonication using a large probe on Fisher sonic dismembranator Model 300 for 3 one minute cycles at 95% relative output. The resulting lysate is centrifuged at 17,500 RPM for 30 minutes at 4° C. To the resulting supernatant is added 2% (w:v) streptomycin sulfate. After incubation for 15 to 30 minutes at 4° C., the lysate is centrifuged at 17,500 RPM as above. The resulting supernatant is adjusted to 30% saturation with ammonium sulfate, incubated for 30 minutes at 4° C., and centrifuged at 17,500 RPM as above. The supernatant is adjusted to 60% saturation with ammonium sulfate, incubated for 30 minutes at 4° C., then centrifuged at 17,500 RPM as above. The pellet formed by the addition of 60% ammonium sulfate is resuspended in 100 mM potassium phosphate buffer, pH 7.0

17 to yield approximately 80 to 100 mg/ml total protein, and is centrifuged at 17,500 RPM as above. The supernatant is termed the crude extract.

Procedure VIII. Avidin Monomer Affinity Chromatography

The crude extract is applied to a 4 mm×5 cm column packed with avidin monomer affinity resin (U.S. Ser. No. 414,785) on a LKB HPLC system equipped with two Model 2150 pumps, Model 2152 controller, and a Model 2140 spectral detector. Sample absorbance is monitored at 280 nm. The crude extract is applied in 100 mM potassium phosphate buffer, pH 6.8 to 7.2 (or other appropriate buffer at a pH of 4.0 to 11.0) at a flow rate of 0.1 ml/min to a column equilibrated with the same buffer. After the sample is loaded, the column is washed with phosphate buffer at a flow rate of 1 ml/min until absorbance returned to the baseline absorbance, and all nonbound material is washed from the resin. The column is then equilibrated with water, followed by application of 5 ml of 2M NaCl. The column is reequilibrated with water. This same NaCl-water wash procedure is repeated four to five times. The sample is eluted using acetic acid or biotin, as detailed in Procedure IX.

Procedure IX. Elution of the Hybrid Polypeptide from the Avidin Monomer Affinity Resin A. Elution using acetic acid Five ml of 10% glacial acetic acid are applied to the column. Eluted hybrid polypeptide is collected until the absorbance at 280 nm returns to the baseline absorbance.

B. Elution using biotin

Five ml of 10 mM biotin in 100 mM potassium phosphate buffer, pH 6.5 is applied to the column. Eluted hybrid polypeptide is collected until the absorbance at 280 nm returns to the baseline absorbance.

Procedure X. Cleavage of the Polypeptide of Interest from the Polypeptide for Attachment A. Acid cleavage Reference: London, M. (1977) *Methods in Enzymology* 47:145–149. The hybrid polypeptide suspension is adjusted to 70% formic acid (v/v) and incubated at 40° C. for 24 to 48 hours. The mixture is then freeze-dried. Highly pure polypeptide of interest is obtained by Procedure VIII.

B. Cyanogen bromide cleavage of methionine residues

Reference: Gross, E. and B. Witkop (1961) *Journal of American Chemical Society* 83:1510–1511.

The hybrid polypeptide is dissolved in 70% (v/v) aqueous formic acid at 23° C. A 50 molar excess of cyanogen bromide is added in a small volume of 70% formic acid, with stirring. The mixture is incubated in the dark under nitrogen at 20–25° C. for 16 to 24 hours. The mixture is then diluted with 10 volumes of water and freeze-dried. Highly pure polypeptide of interest is obtained by Procedure VIII.

Procedure XI. Separation of the Polypeptide of Interest from the Polypeptide for Attachment The dried polypeptide mixture is resuspended in avidin monomer column loading buffer, 100 mM phosphate buffer pH 6.8–7.2, or other appropriate buffer at a pH of between 4.0 and 11.0. Highly pure polypeptide of interest is obtained by passing the cleaved polypeptide mixture over the avidin resin using the procedure described above. The polypeptide for attachment is retained by the avidin monomer and the polypeptide of interest is not retained. The polypeptide of interest is collected in the column flowthrough.

5Procedure XII. Plasmid Expression Vectors

Two plasmids are obtained from D. Samols, Case Western Reserve University.

A. Plasmid ptac 1.3t.

This plasmid contains the DNA sequence coding for the 123 amino acid sequence of the 1.3S polypeptide of transcarboxylase from *Propionibacterium shermanii* (SEQ ID NO:2). The DNA coding for the 1.3S polypeptide is cloned as a 431 base pair fragment into the polylinker region of the expression vector pKK223-3 as described by Murtif et al. (*Proc Nat Acad Sci USA* 82:5617–5621 (1985)). Plasmid ptac1.3(1–125). The plasmid ptac 1.3(1–125) is described by Murtif and Samols, *J Biol Chem* 262:11813–11815 (1987). Like ptac1.3t, ptac1.3(1–125) also contains the 1.3S polypeptide but in addition has the sequence GAT CCA TAA CGC CTA AGC TT (SEQ ID NO:3) at the 3' end of the 1.3S gene that encodes a BamHI restriction endonuclease site. This DNA additional sequence codes for the linking amino acid sequence asp-pro at the carboxyl terminus of the 1.3S polypeptide.

In order to more fully illustrate the nature of this invention and the manner of practicing the same, the following examples are presented. Examples 4, 5, 7, and 8 have not actually been conducted but it is believed that if they were conducted, they would be conducted in the following manner.

EXAMPLE 1

Modification of ptac1.3(1–125) to Increase Hybrid Polypeptide Expression Levels in *E. coli.*

In order to increase the expression level of hybrid polypeptides produced from chimeric genes inserted into ptac1.3(1–125) from approximately 0.1% of total soluble cellular protein to approximately 5.0% of total soluble cell protein, ptac1.3(1–125) was modified as follows. ptac1.3 (1–125) was digested with the restriction enzymes XhoI and HindIII. The desired 131 base pair (bp) fragment was obtained by agarose gel electrophoresis. The vector ptac1.3t was also digested with XhoI and HindIII using the conditions described above, and the 4.86 kilobase (kb) fragment was obtained by agarose gel purification. The plasmid ptac1.3dp (FIG. 1) was obtained by ligation of the 131 bp fragment from ptac1.3(1–125) to the 4.86 kb fragment of ptac1.3t. The ligated plasmid mixture was used to transform competent *E. coli* HB101. An *E. coli* clone harboring ptac1.3dp was identified by restriction enzyme digestion of plasmids isolated from selected ampicillin-resistant *E. coli* cells.

EXAMPLE 2

Fusion of a Polypeptide of Interest to the C-terminus of a Polypeptide for Attachment with an Acid Cleavage Site Between the Polypeptides This example describes a hybrid polypeptide in which a synthetic β-endorphin polypeptide is fused to the carboxyl terminus of the 1.3S polypeptide. An asp-pro cleavage site is incorporated between the two polypeptides for cleavage and subsequent purification of β-endorphin away from the 1.3S polypeptide after affinity purification using avidin monomer resin.

Synthesis of the β-endorphin Gene

The amino acid sequence of a modified β-endorphin polypeptide is shown in SEQ ID NO:6 and the corresponding nucleotide sequence coding for this amino acid sequence is shown in SEQ ID NO:7. The synthetic oligonucleotides from which this synthetic gene was assembled are shown in SEQ ID NO:8 (RHcbe1) and SEQ ID NO:9 (RHcbe2). There are no internal methionine residues in the modified β-endorphin polypeptide. The BamHI endonuclease cleavage recognition sequence GGATCC at nucleotide positions 12 through 17 at the 5' end of SEQ ID NO:6 allows the introducion of an ATG codon at the 5' terminus of the β-endorphin gene when this fragment is introduced into the BamHI site of ptac1.3dp (SEQ ID NO:5), thereby adding a methionine at the N-terminus of the polypeptide. To maximize expression in *E. coli*, the amino acid sequence of authentic β-endorphin was reverse translated into a DNA sequence using preferred codon usages of highly expressed *E. coli* genes (DeBoer, H. and Chapter 8, *Maximizing Gene Expression*, W. Reznikoff and L. Gold, Eds.). RHcbe1 and RHcbe2 were synthesized, annealed and filled by T7 DNA polymerase as described in Procedure VII. The resulting double stranded DNA sequence (SEQ ID NO:5) was digested with BamHI, generating 105 bp fragment coding for the synthetic β-endorphin which was purified by agarose gel electrophoresis. The plasmid vector pUC19 (Sambrook et al, *Molecular Cloning, A Laboratory Manual, 2nd Edition, Vol* 1, 1989. p. 1.13) was linearized with BamHI. The 5' terminus of the linearized plasmid was dephosphorylated prior to ligation by incubating the digest mixture with calf intestinal phosphatase using the protocol described by Sambrook et al (ibid, Vol.1, pp. 3.38–3.39), to minimize self-ligation of the vector. Pure linear plasmid was recovered by agarose gel electrophoresis, and the 110 bp synthetic β-endorphin gene fragment was ligated to the pUC19 plasmid, and this ligated plasmid was used to transform competent *E. coli* HB101. Following plasmid isolation from ampicillin-resistant clones, the recombinant *E. coli* cells harboring the correct plasmid were identified by restriction enzyme digestion. This recombinant plasmid containing the gene for the synthetic β-endorphin was designated pUC19endorB3.

Cloning of synthetic β-endorphin into ptac1.3dp

The β endorphin gene in pUC19endorB3 was fused to the 3' terminus of the 1.3S gene in ptac1.3dp as follows: a 105 bp β-endorphin gene fragment was generated by digestion of pUC19endorB3 with BamHI, and purified by agarose gel electrophoresis. The vector ptac1.3dp, which contains two BamHI sites, was partially digested with BamHI. Plasmid DNA cut at only one BamHI site was purified by agarose gel electrophoresis. The 105 bp β-endorphin gene was ligated into the BamHI site of the linearized ptac1.3dp plasmid and the ligation mixture was used to transform competent *E. coli* HB101. The ligated plasmid containing the endorphin gene in the proper orientation was identified by restriction enzyme analysis of plasmids isolated from ampicillin-resistant transformed *E. coli* and was designated ptac1.3dp:endorB3 (FIG. 2A). This plasmid codes for a hybrid fusion polypetide consisting of the 1.3S polypeptide fused at its carboxyl terminus to an asp-pro cleavage sequence fused to a synthetic β-endorphin polypeptide containing a methionine residue at position 1. A highly pure preparation of the synthetic β-endorphin was obtained by inoculation of L-broth containing 100 mg/l ampicillin with the *E. coli* host harboring ptac1.3dp:endorB3. A crude protein extract containing the 1.3S:βendorphin hybrid polypeptide was obtained by following Procedure VII. Highly pure 1.3S:β-endorphin polypeptide was obtained by avidin monomer affinity chromatography described in Procedure VIII, using acetic acid to elute the purified hybrid polypeptide from the resin (Procedure IX A). Cleavage of β-endorphin from the 1.3S polypeptide was accomplished by incubation in formic acid according to Part A of Procedure X, and highly pure β-endorphin was obtained by avidin monomer affinity chromatography of the cleavage mixture by repeating Procedure XI. Following acid cleavage of an asp-pro linking sequence, a proline residue remains at the N-terminus of the cleaved β-endorphin polypeptide.

Clones containing the β-endorphin gene fragment inserted in the opposite orientation from ptac1.3dp:endorB3 yielded a 1.3S polypeptide fused to a novel 21 amino acid reverse endorphin peptide joined by the linking amino acid sequence asp-pro, The gene designated ptac1.3dp:revendorB3 that encodes this novel peptide is shown in FIG. 2B. This polypeptide could be purified by avidin monomer chromatography (Procedure VIII), eluted in high yield and high purity from the column using acetic acid (Procedure IX A).

This example further demonstrates production of a hybrid polypeptide containing a polypeptide for binding to avidin as an efficacious method for obtaining polypeptides of interest in high yield and high purity.

EXAMPLE 3

Fusion of a Polypeptide of Interest to a Polypeptide for Attachment, with a Methionine Cleavage Site Between the Two Polypeptides In this example, the synthetic β-endorphin polypeptide is fused at its N-terminus to a methionine residue, this methionine residue being positioned at the C-terminus of the 1.3S polypeptide, thus providing a single amino acid cleavage site for separation of β-endorphin from the 1.3S polypeptide following avidin monomer chromatography. Cleavage with cyanogen bromide yields an unmodified N-terminus on β-endorphin, as the methionine is cleaved from the N-terminus of β-endorphin.

The vector ptac1.3dp is digested to completion with XhoI and HindIII, and the 131 bp fragment is purified by agarose gel electrophoresis. This 131 bp fragment is subjected to partial digestion with Sau3A, and the 110 bp fragment so generated is isolated and purified by agarose gel electrophoresis. This XhoI-Sau3A fragment is ligated to a double-stranded synthetic DNA fragment (SEQ ID NO:12) coding for β-endorphin. This β-endorphin has a methionine residue at its N-terminus. This fragment in SEQ ID NO:12 is assembled from synthetic oligonucleotides SEQ ID NO:10 and SEQ ID NO:11 as described in Procedure VI, and is digested to completion with Sau3A prior to ligation to the 110 bp XhoI-Sau3A fragment. The 220 bp product of this ligation is purified by agarose gel electrophoresis. The vector ptac1.3dp is subjected to partial digestion with XhoI and BamHI, and the 4886 bp linear vector is purified by agarose gel electrophoresis. The ligated plasmid is used to transform competent *E. coli* CSH26, prepared according to Procedure IV. Plasmids are isolated from transformed ampicillin-resistant *E. coli* clones, and a plasmid containing the desired gene in the correct orientation is identified by restriction enzyme analysis and designated ptac1.3dp:met:endor (FIG. 2C). A highly pure preparation of the synthetic β-endorphin is obtained by inoculation of L-broth containing 100 mg/l ampicillin with the *E. coli* host harboring ptac1.3:metendor. A crude protein extract containing the 1.3S:β-endorphin hybrid polypeptide is obtained by following Procedure VII. Highly pure 1.3S:β-endorphin polypeptide is obtained by avidin monomer affinity chromatography described in Procedure VIII, using elution with acetic acid to elute the purified hybrid polypeptide from the resin (procedure VIIIA). Cleavage of β-endorphin from the 1.3S polypeptide was accomplished by incubation in cyanogen bromide according to Part B of Procedure X, and highly pure β-endorphin is obtained by avidin monomer affinity chromatography of the cleavage mixture by repeating Procedure XI.

EXAMPLE 4

Fusion of a Polypeptide of Interest Directly to the Carboxyl Terminus of a Polypeptide for Attachment, with no Linking Amino Acid Sequence Being Present in the Hybrid Polypeptide In this example, a synthetic β-endorphin polypeptide is fused directly to the C-terminus of the 1.3S polypeptide. Avidin monomer chromatography is used to obtain highly pure β-endorphin in the form of a hybrid fusion polypeptide.

The construct ptac1.3t (Procedure XII) is digested to completion with XhoI and HindIII, and the smaller 131 bp fragment is purified by agarose gel electrophoresis. This 131 bp fragment is subjected to partial digestion with Sau3A I, and the 110 bp fragment is agarose-gel purified. The 110 bp fragment is ligated to the double stranded DNA fragment SEQ ID NO:15. SEQ ID NO:15 encodes a synthetic β-endorphin gene with no DNA coding for a linking amino acid or amino acid sequence at its 3' terminus. SEQ ID NO:15 is assembled from synthetic oligonucleotides SEQ ID NO:13 and SEQ ID NO:14 using Procedure VI. Prior to ligation to the 110 bp fragment, SEQ ID NO:15 is digested to completion with Sau3A I. The 217 bp ligation product is purified by agarose gel electrophoresis. Vector ptac1.3dp is linearized by partial digestion with XhoI and BamHI, and the 4886 bp fragment is also purified using agarose gel electorphoresis. The ligated plasmid is used to transform competent E. coli CSH26. Recombinant plasmids are isolated from ampicillin-resistant transformants, and a clone containing the desired gene in the correct orientation is identified by restriction enzyme analysis and designated ptac1.3:endor (FIG. 2D). A highly pure preparation of the synthetic β-endorphin is obtained by inoculation of L-broth containing 100 mg/l ampicillin with the E. coli host harboring ptac1.3:endor. A crude protein extract containing the the 1.3S:β-endorphin hybrid polypeptide is obtained by following Procedure VII. Highly pure 1.3S:β-endorphin polypeptide is obtained by avidin monomer affinity chromatography as described in Procedure VIII, using elution with acetic acid to elute the purified hybrid polypeptide from the resin (procedure VIIIA).

EXAMPLE 5
Fusion of Two Polypeptides of Interest to the C-terminus of a Single Polypeptide for Attachment in the Order, Polypeptide for Attachment:Polypeptide of Interest:Polypeptide of Interest In this example, two β-endorphin polypeptides in tandem are fused to the C-terminus of one 1.3S polypeptide, with the linking amino acids asp-pro-met separating the first β-endorphin polypeptide from the C-terminus of the 1.3S polypeptide and another sequence of asp-pro-met separating the first β-endorphin from the second β-endorphin polypeptide. Such a fusion doubles the yield of the polypeptide of interest, at the same time providing a means for purification of that polypeptide by avidin affinity chromatography.

The plasmid ptac1.3dp (FIG. 1) is digested to completion with XhoI and BamHI. The resulting 118 bp fragment that encodes for the sequence beginning at amino acids 8 to the asp-pro site generated by the BamHI site at the 3'terminus of the 1.3S polypeptide as found in SEQ ID NO:5. This fragment is purified by agarose gel electrophoresis. Two tandem β-endorphin polypeptides are generated by the creation of the double-stranded DNA fragments SEQ ID NO:18, assembled from oligonucletides SEQ ID NO:16 and SEQ ID NO:17; and SEQ ID NO:21, assembled from SEQ ID NO:19 and SEQ ID NO:20. SEQ ID NO:18 and SEQ ID NO:21 were assembled from their respective oligonuleotides using the synthesis and strand assembly strategy described in Procedure VI. SEQ ID NO:18 and SEQ ID NO:21 are digested with BamHI and ligated. This fragment codes for two β-endorphin polypeptides in tandem, separated from each other by an asp-pro cleavage sequence. The dimeric product of ligation is purified by agarose gel electrophoresis, and this fragment is ligated to the 118 bp XhoI-BamHI 1.3S partial coding sequence obtained from ptac1.3dp. This ligation product is purified by agarose gel electrophoresis, and is ligated to a 4886 bp fragment generated by partial digestion of ptac1.3dp linearized by partial digestion with XhoI and BamHI. Plasmid DNA is isolated from transformed E. coli HB101. Plasmids containing the correct chimeric gene orientation are confirmed by restriction endonuclease mapping and designated ptac1.3:endor:endor (FIG. 3A). A highly pure preparation of synthetic β-endorphin is obtained by inoculation of L-broth containing 100 mg/l ampicillin with the E. coli host harboring ptac1.3:endor:endor. A crude protein extract containing the the 1.3S:β-endorphin:β-endorphin hybrid polypeptide is obtained by following Procedure VII. Highly pure 1.3S:β-endorphin:β-endorphin polypeptide is obtained by avidin monomer affinity chromatography described in Procedure VIII, using acetic acid to elute the purified hybrid polypeptide from the resin (procedure VIIIA). Cleavage of both β-endorphin polypeptides from the 1.3S polypeptide in a single step is accomplished by incubation in formic acid according to Part A of Procedure X, and highly pure β-endorphin is obtained by avidin monomer affinity chromatography of the cleavage mixture by repeating Procedure XI.

EXAMPLE 6
Fusion of One Polypeptide of Interest to the N-terminus of a Polypeptide for Attachment and Fusion of a Second Polypeptide of Interest to the C-terminus of the Same Polypeptide for Attachment In this example, the maltose binding protein (Guan, C. et al., Gene 67-21-30 (1987) and Maina, et al., Gene 74:365–373 (1988)) was fused to the N-terminus of the 1.3S polypeptide and synthetic β-endorphin was fused to the C-terminus of the same 1.3S polypeptide,. thus creating a hybrid polypeptide consisting of two different noncontiguous polypeptides of interest.

The construct ptac1.3dp:endorB3 (FIG. 2A) was digested with SalI and HindIII. A 438 bp fragment created was purified by agarose gel electrophoresis. This fragment encodes amino acids 19 to 123 of the 1.3S polypeptide, the asp-pro-met linking amino acids, and the 31 amino acid β-endorphin polypeptide. The vector pMAL-c (obtained from New England Biolabs) was linearized by digestion with SalI and HindIII. This vector contains the maltose binding protein under the regulation of the tac promoter (Guan, C. et al., Gene 67-21-30 (1987) and Maina, et al., Gene 74:365–373 (1988)). The linearized vector and the 438 bp 1.3S-β-endorphin fragment were ligated, and the ligation mix was used to transform competent E. coli CHS26. Plasmid DNA was isolated, and plasmids containing the correct chimeric gene orientation were confirmed by restriction endonuclease mapping. The resulting clone was designated ptac:malB:1.3:endorB3 (FIG. 3B). A highly pure preparation of the hybrid maltose binding protein-synthetic β-endorphin polypeptide is obtained by inoculation of L-broth containing 100 mg/l ampicillin with the E. coli host harboring ptac:malB:1.3:endorB3. A crude protein extract containing the hybrid polypeptide is obtained by following Procedure VII. Highly pure maltose binding protein:1.3S:β-endorphin hybrid polypeptide is obtained by avidin monomer affinity chromatography described in Procedure VIII, using biotin to elute the purified hybrid polypeptide from the resin (Procedure VIIIB). Biotin is removed from the polypeptide suspension by dialysis against three changes of 100 mM ammonium carbonate buffer, pH 7.2, followed by freeze-drying of the sample. Cleavage of β-endorphin from the 1.3S polypeptide is accomplished by incubation in cyanogen bromide according to Part B of Procedure X, and highly pure β endorphin is obtained by avidin monomer affinity chromatography of the cleavage mixture by repeating Procedure XI. The maltose-binding protein-1.3S hybrid polypeptide was recovered in highly pure form by repeating the biotin elution procedure described in Procedure VIIIB.

EXAMPLE 7

Fusion of Two Polypeptides of Interest in Tandem to the N-terminus of a Polypeptide for Attachment, with an Amino Acid Cleavage Sequence Separating the First Polypeptide of Interest from the Polypeptide for Attachment, and a Second Amino Acid Cleavage Sequence Separating the First Polypeptide of Interest from the Second Polypeptide of Interest The maltose binding protein and β-endorphin are fused in tandem to the amino-terminus of the 1.3S polypeptide. An amino acid cleavage site separates the maltose binding protein and β-endorphin, and another amino acid cleavage site separates β-endorphin and the 1.3S polypeptide.

The plasmid ptac1.3dp is digested with HincII and HindIII. The 332 bp fragment is purified by agarose gel electrophoresis. Linkers encoding a BamHI recognition sequence (CGGATCCG) are ligated to this fragment, and the fragment is digested with BamHI to generate a BamHI site at the 5'terminus of the fragment. The 338 bp BamHI-HindIII fragment so generated is purified by agarose gel electrophoresis. The DNA fragment SEQ ID NO:15 is digested with BamHI, and is ligated to the 338 bp BamHI-HindIII modified fragment from ptac1.3dp. The desired 444 bp fragment is purified by agarose gel electrophoresis. The vector pMAL-c (New England Biolabs, Beverly, Mass.) is digested to a 6.1 kb fragment with HindIII and BamHI, and the large fragment is purified by agarose gel electrophoresis. The 444 bp fragment and the 6.1 kb fragment are ligated, and the ligation mix is used to transform competent E. coli CSH26. Plasmid DNA is isolated, and plasmids containings the chimeric gene in the correct orientation are confirmed by restriction endonuclease mapping, and are designated ptac:malC:endorB3:1.3dp (FIG. 3C). The correct recombinant plasmid codes for a fusion protein composed of a 42,000 MW maltose binding protein fused by an asp-pro-met linker to β-endorphin joined by an asp-pro linker to amino acids 19–123 of the 1.3S polypeptide having an asp-pro carboxyl terminus. Highly pure maltose binding protein:β-endorphin:1.3S hybrid polypeptide is obtained by avidin monomer affinity chromatography described in Procedure VIII, using biotin to elute the purified hybrid polypeptide from the resin (Procedure VIIIB). Biotin is removed from the polypeptide suspension by dialysis against three changes of 100 mM ammonium carbonate buffer, pH 7.2, followed by freeze-drying of the sample. Cleavage of β-endorphin from the 1.3S polypeptide is accomplished by incubation in formic acid according to Part A of Procedure X, and highly pure β-endorphin is obtained by avidin monomer affinity chromatography of the cleavage mixture by repeating Procedure XI. The maltose binding protein is recovered in highly pure form by elution of the maltose binding protein:1.3S hybrid polypeptide from the avidin monomer resin with biotin using Part B of Procedure IX. The hybrid polypeptide is purified away from the biotin by dialysis against three changes of 100 mM ammonium carbonate buffer, pH 7.2, followed by freeze-drying of the sample. The sample is freeze-dried, and reconstituted in cyanogen bromide according to Part B of Procedure X. The maltose-binding protein is recovered in highly pure form by repeating the avidin monomer chromatography process detailed in Procedure XI. cl EXAMPLE 8

Fusion of Two Polypeptides of Interest to the C-termini of Two Polypeptides for Attachment Within the Same Hybrid Polypeptide In this example, two noncontiguous β-endorphin polypeptides are fused to two noncontiguous 1.3S polypeptides within one hybrid polypeptide with a cleavage amino acid sequence between each 1.3S polypeptide and the β-endorphin to which it is directly linked, producing the fusion hybrid polypeptide 1.3S:asp-pro-met:β-endorphin:asp-pro:1.3S:asp-pro-met:β-endorphin.

The vector 1.3dp:endorB3 (FIG. 2A) is digested with HincII and HindIII and the 437 bp fragment is purified by agarose gel electrophoresis. Synthetic DNA linkers encoding a BamHI recognition sequence, CGGATCCG (New England Biolabs, Inc. Beverly, Mass.) are ligated to this 437 bp fragment. Following ligation, this DNA is subjected to BamHI digestion to generate BamHI cohesive termini, and the 443 bp BamHI-HindIII fragment is purified by agarose gel electrophoresis. The ptac 1.3:endor:endor (FIG. 3A) is partially digested with BamHI and HindIII to yield a linear DNA of 5.1 kb digested at a single BamHI site and also at a single HindIII site. This 5.1 kb fragment is purified by agarose gel electrophoresis, then is ligated to the 443 bp fragment. The ligation mix is used to transform competent *E. coli* HB101. Plasmid DNA is isolated from ampicillin-resistant transformed *E. coli*, and plasmids containing the correct chimeric gene orientation are confirmed by restriction endonuclease mapping. The recombinant plasmid obtained by this procedure is designated ptac1.3:endor:1.3:endor (FIG. 4) and encodes a hybrid polypeptide which permits the isolation of two molecules of β-endorphin for every hybrid polypeptide purified, which may double the yield of polypeptide from a single fermentation. A highly pure preparation of synthetic β-endorphin is obtained by inoculation of L-broth containing 100 mg/l ampicillin with the *E. coli* host harboring ptac1.3:endor:1.3:endor. A crude protein extract containing the 1.3S:β-endorphin:1.3S:β-endorphin hybrid polypeptide is obtained by following Procedure VII. Highly pure 1.3S:β-endorphin:1.3S:β-endorphin polypeptide is obtained by avidin monomer affinity chromatography described in Procedure VIII, using acetic acid to elute the purified hybrid polypeptide from the resin (procedure VIIIA). Cleavage of both β-endorphin polypeptides from both 1.3S polypeptides in a single step is accomplished by incubation in formic acid according to Part A of Procedure X, and highly pure β-endorphin is obtained by avidin monomer affinity chromatography of the cleavage mixture repeating Procedure XI.

As used in the claims, unless indicated otherwise, the term "avidin" includes streptavidin.

While this invention has been described in terms of certain preferred embodiments and illustrated by means of specific exmaples, the invention is not to be construed as limited except as set forth in the following claims.

We claim:

1. A composition of matter comprising at least one polypeptide of interest fused to at least one biotinylated avidin binding polypeptide, wherein the polypeptide of interest and the biotinylated avidin binding polypeptide each have a N-terminus and a C-terminus and the fusion takes place at the C-terminus of the biotinylated avidin binding polypeptide.

2. A composition of matter according to claim 1 wherein one or more linking amino acids in sequence are present for cleaving the polypeptide of interest from the biotinylated avidin binding polylpeptide.

3. A composition of matter according to claim 2 wherein said one or more linking amino acids is fused to said C-terminus of said biotinylated avidin binding polypeptide and the N-terminus of the polypeptide of interest.

4. A composition of matter according to claim 2 wherein said one or more linking amino acids is selected from the class consisting of aspartic acid-proline; asparagine-glycine; methionine; cysteine; lysine-proline; arginine-proline; lysine-arginine; and isoleucine-glutamic acid-glycine-arginine.

5. A composition of matter according to claim 1 wherein said biotinylated avidin binding polypeptide is 1.3S polypeptide subunit of the transcarboxylase from Propionibacterium.

6. A composition of matter according to claim 1 wherein said avidin binding polypeptide is 1.3S having a recognition sequence therein for attachment of biotin.

7. A composition of matter according to claim 1 wherein said biotinylated avidin binding polypeptide contains a recognition sequence consisting of a plurality of Pro Ala Pro Leu Ala Gly Thr Val Ser Lys Ile Leu Val Lys Glu Gly Asp Thr Val Lys Ala Gly Gln Thr Val Leu Val Leu Glu Ala Met Lys Met Glu Thr Glu Ile Asn Ala Pro Thr Asp Gly.

8. A composition according to claim 1 wherein said avidin is monomeric avidin.

9. A composition of matter according to claim 1 wherein said avidin is streptavidin.

10. A composition of matter according to claim 1 wherein said avidin is tetrameric avidin.

11. A composition of matter according to claim 1 wherein said polypeptide of interest is an enzyme.

12. A composition of matter according to claim 1 wherein said polypeptide of interest has anti-tumor activity.

13. A composition of matter according to claim 1 wherein said polypeptide of interest is an antigen useful for vaccine production.

14. A composition of matter according to claim 1 wherein said polypeptide of interest has an amino acid sequence for recognition of antigens.

15. A composition of matter according to claim 1 wherein said polypeptide of interest functions as a diagnostic reagent.

16. A composition of matter according to claim 1 wherein there is present a plurality of biotinylated avidin binding polypeptides and each individual biotinylated avidin binding polypeptide is separated by at least one polypeptides of interest.

17. A composition of matter according to claim 1 wherein there is present a plurality of polypeptides of interest and each individual polypeptide of interest is separated by at least one biotinylated avidin binding polypeptide.

18. A composition of matter according to claim 1 wherein there is present a plurality of polypeptides of interest.

19. A composition of matter according to claim 18 wherein the plurality of polypeptides of interest are separated by one or more linking amino acids in sequence.

20. A composition of matter according to claim 1 wherein there is present at least two different biotinylated avidin binding polypeptides.

21. A composition of matter according to claim 17 wherein each of the polypeptides of interest comprising said plurality of polypeptides of interest is compositionally identical.

22. A composition of matter according to claim 16 wherein the C-terminus of at least one of the biotinylated avidin binding polypeptides is fused to the N-terminus of a first polypeptide of interest and the N-terminus of another biotinylated avidin binding polypeptide is fused to the C-terminus of the first polypeptide of interest.

* * * * *